(12) United States Patent
Fishman

(10) Patent No.: US 11,027,149 B2
(45) Date of Patent: Jun. 8, 2021

(54) HYBRID ULTRASOUND-GUIDED SUPERFICIAL RADIOTHERAPY SYSTEM AND METHOD

(71) Applicant: Sensus Healthcare, Inc., Boca Raton, FL (US)

(72) Inventor: Kalman Fishman, Boca Raton, FL (US)

(73) Assignee: SENSUS HEALTHCARE, INC., Boca Raton, FL (US)

(*) Notice: Subject to any disclaimer, the term of this patent is extended or adjusted under 35 U.S.C. 154(b) by 541 days.

(21) Appl. No.: 13/740,181

(22) Filed: Jan. 12, 2013

(65) Prior Publication Data

US 2013/0217947 A1    Aug. 22, 2013

Related U.S. Application Data

(60) Provisional application No. 61/586,030, filed on Jan. 12, 2012.

(51) Int. Cl.
*A61B 8/00* (2006.01)
*A61N 5/10* (2006.01)
(Continued)

(52) U.S. Cl.
CPC ............ *A61N 5/1039* (2013.01); *A61B 8/085* (2013.01); *A61B 8/13* (2013.01); *A61B 8/483* (2013.01);
(Continued)

(58) Field of Classification Search
CPC .......... A61B 8/08; A61B 8/13; A61B 8/4405; A61B 8/466; A61B 8/483; A61B 8/565;
(Continued)

(56) References Cited

U.S. PATENT DOCUMENTS 5,703,922 A    12/1997  Rattner
6,637,936 B2 * 10/2003  Crain et al. .................. 378/197
(Continued)

FOREIGN PATENT DOCUMENTS

DE    19520748 A1    12/1996
EP    2292299 A1    3/2011
(Continued)

OTHER PUBLICATIONS

"TOPEX announces sale of skin cancer business operations to SENSUS Healthcare", News Medical, Published Aug. 19, 2010, accessed online Nov. 12, 2014.*
(Continued)

*Primary Examiner* — Christopher L Cook
(74) *Attorney, Agent, or Firm* — Fox Rothschild LLP

(57) ABSTRACT

Systems, method and devices for detecting, analyzing and treating lesions, such as skin cancer are disclosed. Such a system can include a high-frequency ultrasound imaging device to image a lesion. The system can also include a processor that executes instructions stored in memory to perform operations, and the operations can include receiving a plurality of images of the lesion from the high-frequency ultrasound imaging device, rendering a three dimensional model of the lesion using the plurality of images from the high-frequency ultrasound imaging device and determining a treatment dosimetry based on the three dimensional model of the lesion. The system can also include a radiotherapy device to provide radiotherapy treatment to the lesion, where the radiotherapy treatment is based on the treatment dosimetry.

21 Claims, 10 Drawing Sheets

(51) Int. Cl.
*A61B 8/13* (2006.01)
*A61B 8/08* (2006.01)

(52) U.S. Cl.
CPC ............ *A61B 8/565* (2013.01); *A61N 5/1049* (2013.01); *A61N 5/1077* (2013.01); *A61B 8/4405* (2013.01); *A61B 8/466* (2013.01); *A61N 2005/1058* (2013.01)

(58) Field of Classification Search
CPC .......... A61N 2005/1058; A61N 5/1039; A61N 5/1049; A61N 5/1077
See application file for complete search history.

(56) References Cited

U.S. PATENT DOCUMENTS

| | | | |
|---|---|---|---|
| 7,009,194 B2* | 3/2006 | Merlo | G21K 1/02 250/505.1 |
| 7,263,170 B2 | 8/2007 | Pellegrino | |
| 2004/0024300 A1 | 2/2004 | Graf | |
| 2005/0056791 A1 | 3/2005 | Donaghue et al. | |
| 2005/0173648 A1 | 8/2005 | Schmidt et al. | |
| 2005/0251029 A1 | 11/2005 | Khamene et al. | |
| 2007/0076847 A1* | 4/2007 | Pellegrino et al. | 378/97 |
| 2007/0076851 A1* | 4/2007 | Pellegrino | 378/157 |
| 2008/0081998 A1* | 4/2008 | Pan | A61B 8/13 600/458 |
| 2008/0132787 A1 | 6/2008 | Putaala | |
| 2008/0212738 A1* | 9/2008 | Gertner et al. | 378/65 |
| 2010/0246766 A1* | 9/2010 | Kindlein et al. | 378/65 |
| 2011/0057124 A1 | 3/2011 | Rietzel | |
| 2011/0182411 A1* | 7/2011 | Shinagawa et al. | 378/65 |
| 2012/0163539 A1* | 6/2012 | van der Veen et al. | 378/65 |

FOREIGN PATENT DOCUMENTS

| | | |
|---|---|---|
| GB | 2421572 A | 6/2006 |
| WO | 2009075714 A1 | 6/2009 |

OTHER PUBLICATIONS

Vlad et al., "Evaluating the extent of cell death in 3D high frequency ultrasound by registering with whole-mount tumor histopathology", Med. Phys. 37 (8), Aug. 2010, pp. 4288-4297.*
SRT 100 Brochure, Santax Medico, accessed online Nov. 12, 2014.*
Baily et al., "A new technique for radiation shielding in superficial X-ray therapy", British Journal of Radiology, 1981.*
Hildegard Schmid et al., "Ultrasound scanning in Dermatology", 2005.*
Finger et al., "High-Frequency Ultrasound Characteristics of 24 Iris and Iridociliary Melanomas", Arch Ophthalmol, 2007.*
Ying, "Update of Radiotherapy for Skin Cancer", Reveiw Articles, Hong Kong Dermatology & Venereology Bulletin, vol. 9, No. 2, Jun. 2001.*
Jasaitiene et al., "Principles of high-frequency ultrasonography for investigation of skin pathology", JEADV, first published Sep. 16, 2010, also in vol. 25, issue 4, Apr. 2011.*
Patent Cooperation Treaty, "Partial International Search Report of the International Searching Authority,", document of 2 pages, dated Jul. 11, 2013.
Wang et al., "3D Ultrasound-based Patient Positioning for Therapy," Proceedings of SPIE, vol. 6141, Jan. 1, 2006, pp. 61411K-61411K9.
Francescatti et al., "Single Fraction Breast IORT Utilizing Xoft Electronic Brachytherapy," Poster presented at the 6th International Conference of the ISIORT, Scottsdale, AZ, Oct. 14-16, 2010, http://www.xoftinc.com/assets/pdf/posters/Poster_52.pdf.
Reitsamer et al., "Accelerated Partial Breast Irradiation After Conservative Surgery for Breast Cancer," Ann Surg. Jul. 2005; 242(1): 147-148, http://www.ncbi.nlm.nih.gov/pmc/articles/PMC1357716/.
Keen, "Electronic brachytherapy suits APBI, IORT," MedicalPhysicsWeb.Org, Oct. 7, 2010, 4 pages, http://medicalphysicsweb.org/cws/article/research/43968.
Fournier et al., "In Vivo Normal Human Dermis Characterization by 20-MHz Ultrasound Backscatter," IEEE Ultrasonic Symposium proceedings, 1303-06 2000.
Guittet et al., "In Vivo High-Frequency Ultrasonic Characterization of Human Dermis," IEEE Transactions on Biomedical Engineering, 46(6), 740-746, 1999.
Lebertre et al., "Spatial variation of acoustic parameters in human skin: an in vitro study between 22 and 45 MHz," Ultrasound in Medicine & Biology, 28, 599-615 (2002).
Raju et al., "Quantitative ultrasonic methods for characterization of skin lesions in vivo," Ultrasound in Medicine & Biology, 29, 825-838 (2003).
Dyson et al., "Wound healing assessment using 20 MHz ultrasound and photography," Skin Research and Technology 2003; 9: 116-121.
Wortsman et al., "Clinical usefulness of variable frequency ultrasound in localized lesions of the skin," J Am Acad Dermatol 2010; 62 : 247-256.
Wilder et al. "Basal Cell Carcinoma Treated With Radiation Therapy," Nov. 15, 1991;68(10):2134-7.
Olschewski et al., "Radiotherapy of Basal Cell Carcinoma of the Face and Head: Importance of Low Dose per Fraction on Long-Term Outcome," J Dtsch Dermatol Ges. Feb. 2006; 4(2):101-2.
Locke et al., "Radiotherapy for Epithelial Skin Cancer". Jan. 1, 2001.
Childers et al., "Long-Term Results of Irradiation for Basal Cell Carcinoma of the Skin of the Nose," Plast Reconstr Surg. May 1994; 93(6):1169-73.
Abraham et al., "Basal Cell Carcinoma of the Medial Canthal Region," Am J Surg. Oct. 1973; 126(4):492-5.
Caccialanza et al., "Radiotherapy of Carcinomas of the Skin Overlying the Cartilage of the Nose: Our Experience in 671 Lesionsk," J Eur Acad Dermatol Venereol. Sep. 2009; 23(9):1044-9. Epub Apr. 2, 2009.
Kwak et al.; "Solid-state detector design for mobile cargo container inspection system using medium energy X-ray," Nov. 10-16, 2002. 475-479 vol. 1.
Casagrande et al., "High Resolution Digital Flat-Panel X-Ray Detector-Performance and NDT Applications," Thomson Tubes Electroniques 38430 Moirans France, 2000: Roma 2000 15th WCNDT.
Kuhls-Gilcrist et al., "The Solid State X-Ray Image Intensifier (SSXII) in Single Photon Counting (SPC) Mode," Proc SPIE. Mar. 22, 2010; 7622(76221P). pii: 76221P (2010).
Takahashi et al., "Highly Stable Solid-State X-Ray Detector Array," Med Phys. Sep.-Oct. 1992; 19(5):1161-6.
Patent Cooperation Treaty, "International Search Report and Written Opinion of the International Searching Authority," document of 18 pages, dated Oct. 9, 2013.

* cited by examiner

| DOSE/ FRACTION (cGY) | TDF TABLE TIME DOSE FRACTIONATION FACTORS FOR FOUR FRACTIONS PER WEEK TDF# BETWEEN 90 AND 110 FOR NSMC SKIN LESIONS- NUMBER OF FRACTIONS |||||||||||||||||||
|---|---|---|---|---|---|---|---|---|---|---|---|---|---|---|---|---|---|---|---|
| | 4 | 5 | 6 | 8 | 10 | 12 | 14 | 15 | 16 | 18 | 20 | 22 | 24 | 25 | 26 | 28 | 30 | 32 | 34 | 35 | 36 | 40 |
| 20 | 0 | 0 | 1 | 1 | 1 | 1 | 1 | 1 | 1 | 2 | 2 | 2 | 2 | 2 | 2 | 3 | 3 | 3 | 3 | 3 | 3 | 4 |
| 40 | 1 | 1 | 2 | 2 | 3 | 3 | 4 | 4 | 4 | 5 | 5 | 6 | 6 | 7 | 7 | 8 | 8 | 9 | 9 | 9 | 10 | 11 |
| 60 | 2 | 3 | 3 | 4 | 5 | 6 | 7 | 8 | 8 | 9 | 10 | 11 | 12 | 13 | 13 | 14 | 15 | 16 | 17 | 18 | 18 | 20 |
| 80 | 3 | 4 | 5 | 6 | 8 | 9 | 11 | 12 | 13 | 14 | 16 | 17 | 19 | 20 | 20 | 22 | 23 | 25 | 27 | 27 | 28 | 31 |
| 100 | 4 | 6 | 7 | 9 | 11 | 13 | 15 | 17 | 18 | 20 | 22 | 24 | 26 | 28 | 29 | 31 | 33 | 35 | 37 | 39 | 40 | 44 |
| 110 | 5 | 6 | 8 | 10 | 13 | 15 | 18 | 19 | 20 | 23 | 26 | 28 | 31 | 32 | 33 | 36 | 36 | 41 | 43 | 45 | 46 | 51 |
| 120 | 6 | 7 | 9 | 12 | 15 | 18 | 20 | 22 | 23 | 26 | 29 | 32 | 35 | 36 | 38 | 41 | 44 | 47 | 50 | 51 | 53 | 58 |
| 130 | 7 | 8 | 10 | 13 | 16 | 20 | 23 | 25 | 26 | 30 | 33 | 36 | 40 | 41 | 43 | 46 | 49 | 53 | 56 | 58 | 59 | 66 |
| 140 | 7 | 9 | 11 | 15 | 18 | 22 | 26 | 28 | 30 | 33 | 37 | 41 | 44 | 46 | 48 | 52 | 55 | 59 | 63 | 65 | 67 | 74 |
| 150 | 8 | 10 | 12 | 16 | 21 | 25 | 29 | 31 | 33 | 37 | 41 | 45 | 49 | 51 | 53 | 58 | 62 | 66 | 70 | 72 | 74 | 82 |
| 160 | 9 | 11 | 14 | 18 | 23 | 27 | 32 | 34 | 36 | 41 | 45 | 50 | 54 | 57 | 59 | 64 | 68 | 73 | 77 | 79 | 82 | 91 |
| 170 | 10 | 12 | 15 | 20 | 25 | 30 | 35 | 37 | 10 | 45 | 50 | 55 | 60 | 62 | 65 | 70 | 75 | 80 | 85 | 87 | 90 | 100 |
| 180 | 11 | 14 | 16 | 22 | 27 | 33 | 38 | 41 | 44 | 49 | 54 | 60 | 65 | 68 | 71 | 76 | 82 | 87 | 93 | 95 | 98 | 109 |
| 190 | 12 | 15 | 18 | 24 | 30 | 35 | 41 | 44 | 47 | 53 | 59 | 65 | 71 | 74 | 77 | 83 | 89 | 95 | 101 | 103 | 106 | 118 |
| 200 | 13 | 16 | 19 | 26 | 32 | 38 | 45 | 48 | 51 | 58 | 64 | 70 | 77 | 80 | 83 | 90 | 96 | 102 | 109 | 112 | 115 | 128 |
| 210 | 14 | 17 | 21 | 28 | 34 | 41 | 48 | 52 | 55 | 62 | 69 | 76 | 83 | 86 | 90 | 97 | 103 | 110 | 117 | 121 | 124 | 138 |
| 220 | 15 | 19 | 22 | 30 | 37 | 44 | 52 | 56 | 59 | 67 | 74 | 82 | 89 | 93 | 96 | 104 | 111 | 119 | 126 | 130 | 133 | 148 |
| 230 | 16 | 20 | 24 | 32 | 40 | 48 | 56 | 60 | 63 | 71 | 79 | 87 | 95 | 99 | 103 | 111 | 119 | 127 | 135 | 139 | 143 | 159 |
| 240 | 17 | 21 | 25 | 34 | 42 | 51 | 59 | 64 | 68 | 76 | 85 | 93 | 102 | 106 | 110 | 119 | 127 | 136 | 144 | 148 | 152 | |
| 250 | 18 | 23 | 27 | 35 | 45 | 54 | 63 | 68 | 72 | 81 | 90 | 99 | 108 | 113 | 117 | 126 | 135 | 144 | 153 | 158 | | |
| 260 | 19 | 24 | 29 | 38 | 48 | 57 | 67 | 72 | 77 | 86 | 96 | 105 | 115 | 120 | 125 | 134 | 144 | 153 | | | | |
| 270 | 20 | 25 | 30 | 41 | 51 | 61 | 71 | 76 | 81 | 91 | 102 | 112 | 122 | 127 | 132 | 142 | 152 | | | | | |
| 280 | 21 | 27 | 32 | 43 | 54 | 64 | 75 | 81 | 86 | 97 | 107 | 118 | 129 | 134 | 140 | 150 | 161 | | | | | |
| 290 | 23 | 28 | 34 | 45 | 57 | 68 | 79 | 85 | 91 | 102 | 113 | 125 | 136 | 142 | 147 | 159 | | | | | | |
| 300 | 24 | 30 | 36 | 48 | 60 | 72 | 84 | 90 | 96 | 107 | 119 | 131 | 143 | 149 | 155 | | | | | | | |
| 320 | 26 | 33 | 40 | 53 | 68 | 79 | 92 | 99 | 105 | 119 | 132 | 145 | 158 | 165 | | | | | | | | |
| 340 | 29 | 36 | 43 | 58 | 72 | 87 | 101 | 109 | 116 | 130 | 145 | 159 | | | | | | | | | | |
| 360 | 32 | 40 | 47 | 63 | 79 | 95 | 111 | 119 | 125 | 142 | 158 | | | | | | | | | | | |
| 380 | 34 | 43 | 52 | 69 | 85 | 103 | 120 | 129 | 137 | 155 | | | | | | | | | | | | |
| 400 | 37 | 46 | 56 | 74 | 93 | 112 | 130 | 139 | 149 | 167 | | | | | | | | | | | | |
| 420 | 40 | 50 | 60 | 80 | 100 | 120 | 140 | 150 | 160 | | | | | | | | | | | | | |
| 440 | 43 | 54 | 65 | 86 | 108 | 129 | 151 | | | | | | | | | | | | | | | |
| 460 | 46 | 58 | 69 | 92 | 115 | 138 | 161 | | | | | | | | | | | | | | | |
| 480 | 49 | 61 | 74 | 98 | 123 | 148 | 172 | | | | | | | | | | | | | | | |
| 500 | 52 | 65 | 79 | 105 | 131 | 157 | | | | | | | | | | | | | | | | |
| 520 | 56 | 70 | 83 | 111 | 139 | 167 | | | | | | | | | | | | | | | | |
| 540 | 59 | 74 | 88 | 118 | 147 | 177 | | | | | | | | | | | | | | | | |
| 560 | 62 | 78 | 94 | 125 | 156 | | | | | | | | | | | | | | | | | |
| 580 | 66 | 82 | 99 | 132 | 165 | | | | | | | | | | | | | | | | | |
| 600 | 69 | 87 | 104 | 139 | 173 | | | | | | | | | | | | | | | | | |
| 700 | 88 | 110 | 132 | 176 | | | | | | | | | | | | | | | | | | |
| 800 | 108 | 135 | 162 | | | | | | | | | | | | | | | | | | | |
| 900 | 129 | 162 | | | | | | | | | | | | | | | | | | | | |
| 1000 | 152 | | | | | | | | | | | | | | | | | | | | | |

FIG. 4B

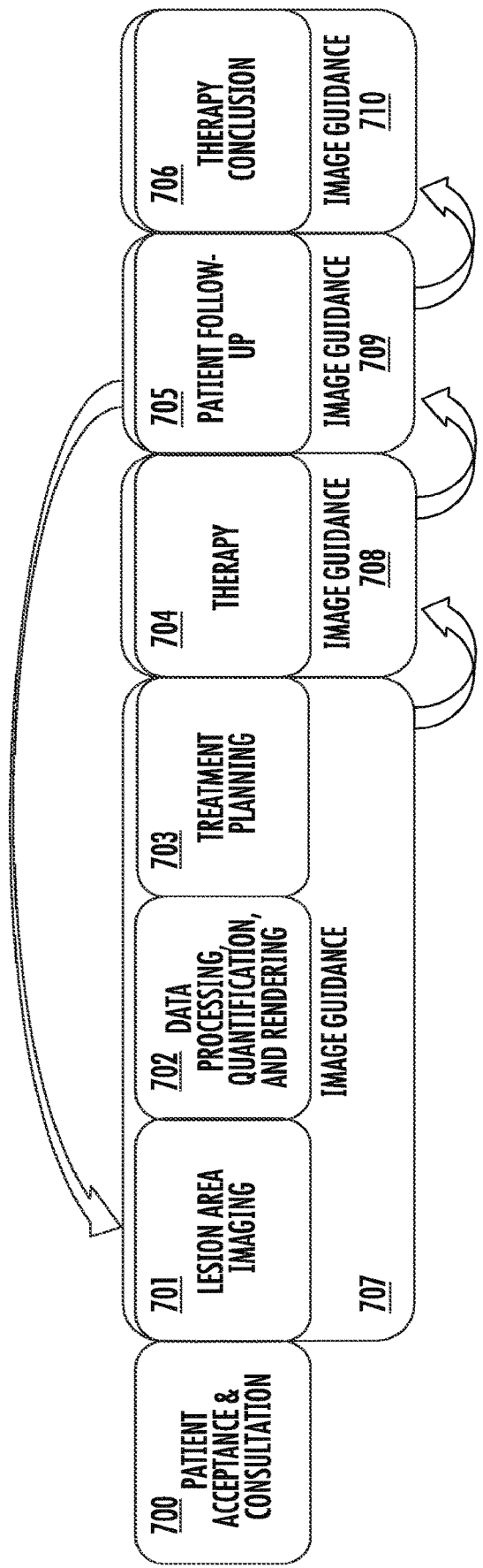

NORMAL SKIN

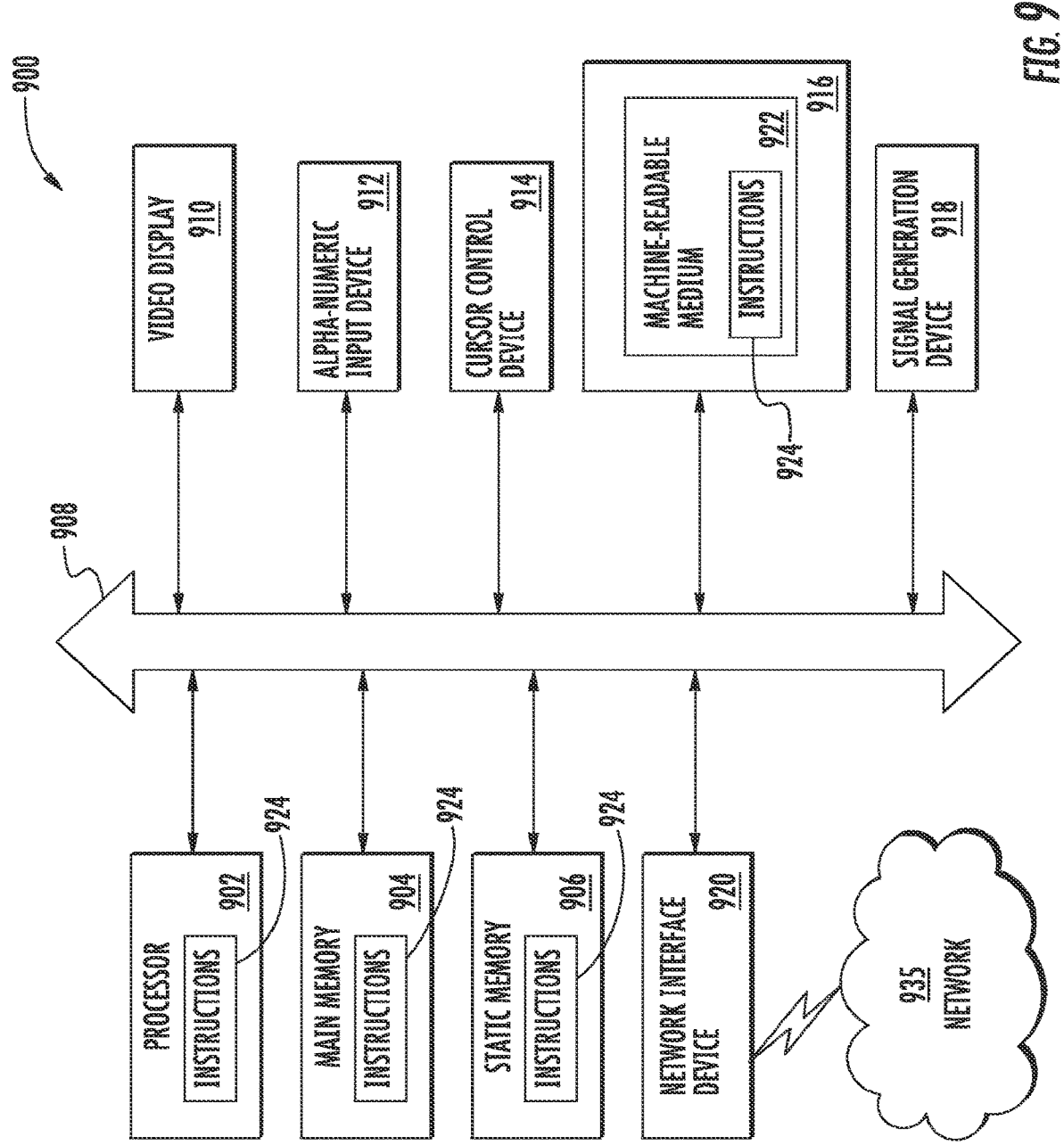

HYBRID ULTRASOUND-GUIDED SUPERFICIAL RADIOTHERAPY SYSTEM AND METHOD

CROSS REFERENCE TO RELATED APPLICATIONS

This patent application claims the benefit of U.S. Provisional Patent Application No. 61/586,030, filed Jan. 12, 2012, which is incorporated by reference in its entirety.

FIELD OF THE INVENTION

The disclosure relates to systems, devices and methods for detecting and treating skin conditions such as skin cancers; more particularly it relates to ultrasound detection of skin cancers and superficial radiotherapy treatment thereof.

BACKGROUND

Skin cancer is the abnormal growth of cells in the skin, and is the most commonly diagnosed type of cancer. The three most common malignant skin cancers are basal cell cancer, squamous cell cancer, and melanoma, each of which is named after the type of skin cell from which it arises. The chances of surviving skin cancer increase if it is detected early and treated appropriately. The present disclosure relates to advances in detection and treatment.

SUMMARY

The system and method provide an integrated image-guided superficial radiotherapy platform, which can be implemented as one integral system with dedicated and mission-specific workflows and controls. The imaging component is provided by high frequency ultrasound. The radiotherapy device, with integrated components, allow a user to obtain real-time radiation beam profile characterization, measurement, and accurate definition over time to assure beam output fidelity and reproducibility. This system and method streamline treatment protocol, provide better outcomes to patients, physicians, and the healthcare system alike through more accurate therapy delivery, timelier therapy spans, reducing and even eliminating the need for invasive biopsy and reconstructive procedures.

In one embodiment, a system for radiation treatment is provided. The system can include a high-frequency ultrasound imaging device to image a lesion. The system can also include a processor that executes instructions stored in memory to perform operations, and the operations can include receiving a plurality of images of the lesion from the high-frequency ultrasound imaging device, rendering a three dimensional model of the lesion using the plurality of images from the high-frequency ultrasound imaging device and determining a treatment dosimetry based on the three dimensional model of the lesion. The system can also include a radiotherapy device to provide radiotherapy treatment to the lesion, where the radiotherapy treatment is based on the treatment dosimetry. The system can also include a moveable base unit, where the high-frequency ultrasound imaging device, the processor that executes instructions stored in memory to perform operations and the radiotherapy device are at least partially housed by the base unit.

In one arrangement, the system can include an articulating treatment arm mounted to the moveable base unit for positioning the radiotherapy device for targeted emission of radiation. The system may also include a camera provided by the articulating arm, a laser pointer provided by the radiotherapy device where the camera and laser pointer provide a video-laser positioning system.

In another embodiment, the system can also include a solid-state x-ray detector array housed within the radiotherapy device to sense characteristics of the radiation emitted by the x-ray tube. Additionally, further operations of the system can include testing the radiotherapy device with the solid-state x-ray detector array, determining characteristics of radiation emitted by the x-ray tube based on the testing of the radiotherapy device and adjusting the radiotherapy device based on characteristics of the radiation emitted by the x-ray tube.

In another embodiment, a system for radiation treatment, can include a memory that stores instructions and a processor that executes the instructions to perform operations. The operations can include receiving a plurality of images of a lesion from the high-frequency ultrasound imaging device, rendering a three dimensional model of the lesion using the plurality of images from the high-frequency ultrasound imaging device, determining a treatment dosimetry based on the three dimensional model of the lesion and providing the treatment dosimetry for use with a radiotherapy device. The operations of the system can also include receiving solid-state x-ray detector array testing data of the radiotherapy device and determining characteristics of radiation emitted by the x-ray tube based on the testing of the radiotherapy device. The operations can also include adjusting the radiotherapy device based on characteristics of the radiation emitted by the x-ray tube.

In one arrangement, the system operations can also include rendering a plurality of two-dimensional images of cross sections of the lesion. Additionally, the system operations can include determining an edge of the lesion and determining a volume of the lesion. Further, the system operations can include determining a treatment voxel for a volume with the lesion to be treated.

In another embodiment, a computer-readable device comprising instructions, which when executed by a processor, can cause the processor to perform operations. The operations can include receiving a plurality of images of a lesion from the high-frequency ultrasound imaging device, rendering a three dimensional model of the lesion using the plurality of images from the high-frequency ultrasound imaging device, determining a treatment dosimetry based on the three dimensional model of the lesion and providing the treatment dosimetry for use with a radiotherapy device. The operations can also include receiving solid-state x-ray detector array testing data of the radiotherapy device and determining characteristics of radiation emitted by the x-ray tube based on the testing of the radiotherapy device. Further the options can include adjusting the radiotherapy device based on characteristics of the radiation emitted by the x-ray tube and rendering a plurality of two-dimensional images of cross sections of the lesion. Also, the operations can include determining an edge of the lesion, determining a volume of the lesion and determining a treatment voxel for a volume with the lesion to be treated.

In yet another embodiment, a method of treating lesions can include obtaining a plurality of images of a lesion with a high-frequency ultrasound device, processing, by utilizing instructions stored in memory and executed by a processor, the plurality of images of the lesion obtained with the high-frequency ultrasound device, analyzing the processed plurality of images of the lesion and providing a targeted radiotherapy to the lesion based on the analysis of the processed plurality of images of the lesion. The method can also include obtaining a plurality of post radiotherapy treatment images of the lesion with a high-frequency ultrasound device after providing targeted radiotherapy to the lesion and during a treatment period of time and providing further targeted radiotherapy to the lesion based on the plurality of post radiotherapy treatment images of the lesion.

In another arrangement, providing a targeted radiotherapy to the lesion based on the analysis of the processed plurality of images of the lesion, can include a plurality of sessions of providing a targeted radiotherapy to the lesion over the treatment period of time. The method can also include analyzing topography of the lesion intermittently during the treatment period of time. The method can further include analyzing volume of the lesion intermittently during the treatment period of time and determining a treatment voxel for a volume with the lesion to be treated.

In one embodiment, a radiotherapy device, can include an x-ray tube housing of an x-ray tube that emits radiation, a retractable support structure provided within the x-ray tube housing, the retractable support structure moveable between an x-ray testing position and a non-testing position, and an x-ray imaging array detector coupled to the retractable support structure where the x-ray imaging array detector in the x-ray testing position senses characteristics of the radiation emitted by the x-ray tube. In one arrangement, the x-ray detector array can be a solid-state x-ray detector array. The characteristics of the radiation emitted by the x-ray tube can indicate misalignment of the x-ray tube or x-ray tube port. Still further, the radiotherapy device can include a memory that stores instructions and a processor that executes the instructions to perform operations, and the operations can include analyzing beam shape integrity of the radiation emitted from the x-ray tube and determining beam shape of the radiation emitted from the x-ray tube.

BRIEF DESCRIPTION OF THE DRAWINGS

FIG. 4B is an exemplary radiotherapy dosage table.

FIG. 7 is a flow diagram of a process of treating a patient.

FIG. 9 is a diagrammatic representation of a machine in the form of a computer system within which a set of instructions, when executed, may cause the machine to perform any one or more of the methodologies discussed herein.

DETAILED DESCRIPTION

Figure 1:
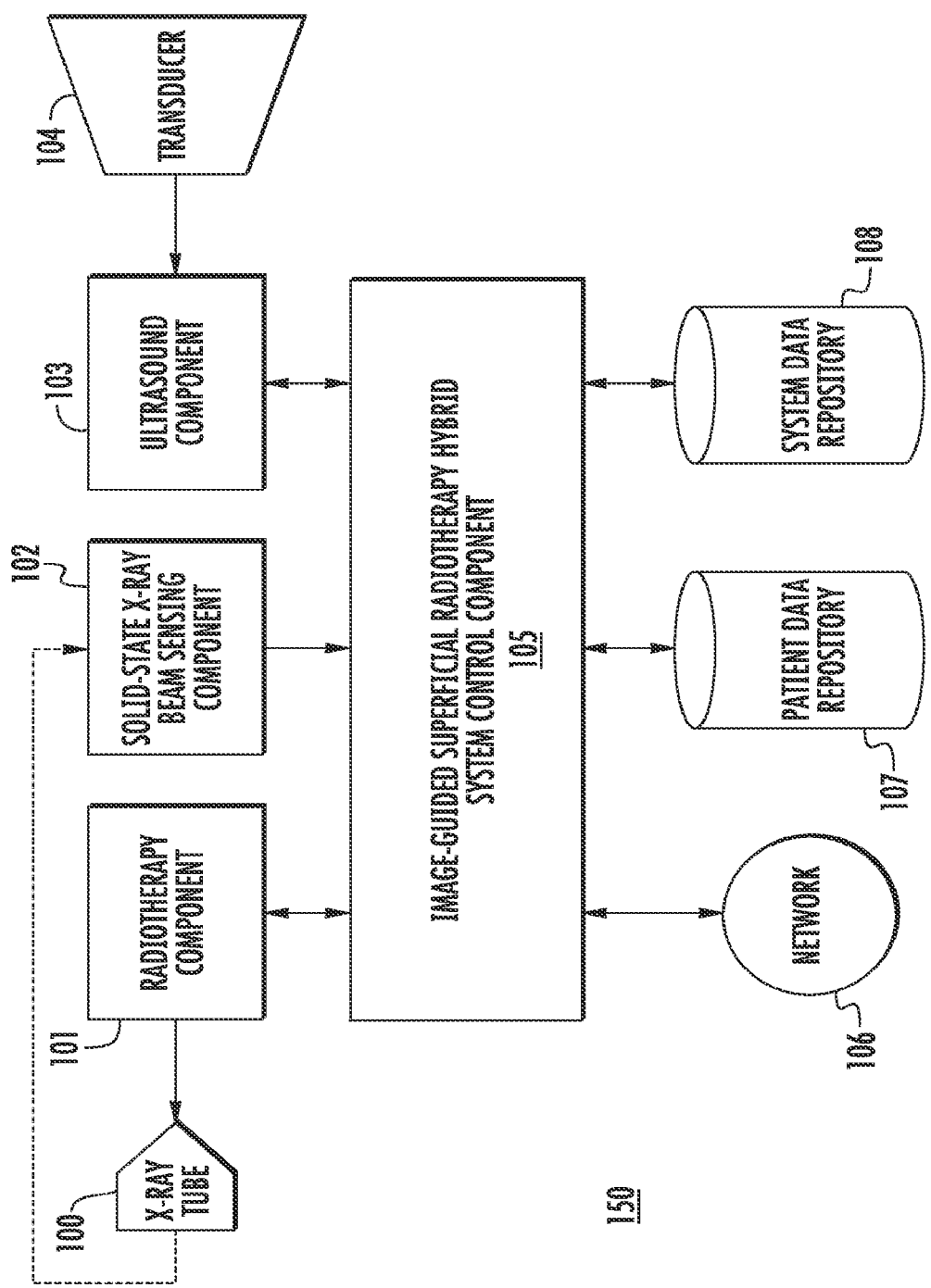
FIG. 1 is a schematic of a high level overview of the components of the system and used in the methods described herein.

Referring to the drawings, the system can deliver both diagnostic and therapeutic functionalities through a single platform and an integrated workflow to better serve and benefit the practitioner and patient with skin cancer and/or skin lesions. The system provides an imaging device and a radiotherapy device used cooperatively to diagnose, treat and verify treatment. Thus, the system can be a hybrid image-guided superficial radiotherapy treatment system. The system includes software to analyze data and images produced by the imaging device to provide pinpoint and focused treatment with the radiotherapy device. Additionally, the diagnostic protocols can be repeated throughout the treatment process to adjust, focus, increase or decrease radiotherapy as appropriate.

FIG. 1 illustrates a high level view of system 150 and its four main sub-modules. The system can include a radiotherapy component 101 with X-ray tube 100, a solid-state X-ray beam sensing component 102, an ultrasound component 103 with a transducer 104, a system control component 105 for guiding the radiotherapy of the radiotherapy component 101 based on images and data obtained from the ultrasound component 103 and transducer 104. The system control component 105 can also work with the solid-state X-ray beam sensing component 102 to ensure that the radiotherapy is of the appropriate intensity, depth and size.

The ultrasound component 103 can include control circuitry, system drivers, operation control software, and a transducer 104, which can be high frequency ultrasonic transducer, for superficial epidermis, dermis-level and/or subcutaneous tissue anatomical imaging. The ultrasound component 103 communicate with the software of the system control component 105 via a bus and system drivers.

The radiotherapy component 101, which can be superficial radiotherapy component, and X-ray tube 100, can together include control circuitry, one or more cooling elements for the x-ray tube, power supplies, one or more high voltage generator, one or more interchangeable aluminum (Al) filter magazines, one or more collimating applicators, and one or more hardware timers that work in concert with a software timer for redundancy and other purposes.

The solid-state X-ray beam sensing component 102 can monitor the beam output of the radiotherapy component 101 and x-ray tube 101, along with overall system stability and yield. The solid-state X-ray beam sensing component 102 is mounted underneath the X-Ray tube 100 and is moved in front of the tube when the system 150 needs to be tested for quality control, or overall system 150 diagnosis purposes. Otherwise, it is retracted back in its home position, away from the X-Ray Tube 100 and the x-ray beam in order not to interfere during a normal operating mode.

In operation, the system 150 utilizes the high frequency ultrasound component 103 with a transducer 104 to scan and image basal cell (BCC) and squamous cell (SCC) lesions. After the lesions have been scanned and imaged by the system 150, the data is processed by the system's software. The software can analyze and quantify the tumor and subsequently prepare a treatment plan that is derived from the actual tumor parameters, such as volume, circumference, penetration depth, and tissue density. Once the tumor analysis and quantification are complete, the system 150 software provides analytical guidance to deliver the most accurate and appropriate superficial radiotherapy pertaining to the scanned and analyzed tumor. The therapy is then delivered by the integrated superficial radiotherapy component 101. The system's software documents the entire diagnosis and treatment cycle and archives the patient data on a patient data repository 107 and the overall system 150 functionality log on a system data repository 108.

The superficial radiotherapy component 101 can be utilized to treat any tumors, lesions or areas where analysis or diagnosis determines that treatment is needed. The superficial radiotherapy component 101 delivers collimated and focused x-ray photon particles to treatment areas. The treatment can be without any biopsies and the pre-treatment analysis, treatment and post-treatment analysis can be carried out locally without the need for remote sources or analysis. The level of treatment can be determined as set forth below.

The system 150 is controlled and operated by the system control component 105, which can include a central computer with a motherboard that runs operation and control software with various parallel and connected boards that allow it to control, communicate, and monitor the various sub-components and modules of the system 150. This achieves harmonious functionality between the two main clinical components of the system 150, the superficial radiotherapy component 101, which provides radiotherapy treatment, and the ultrasound component 103, which is utilized to scan and acquire the anatomy and topology of a patient's skin area of concern for further analysis, diagnosis, quantification, and therapy planning purposes. The system control component 105 can be connected with data repositories, including a patient data repository 107 and a system data repository 108. The system 150 can also be connected to a network 106, such as a local area network, a wide area network and/or the Internet, which allows for clinical and system data exchange with remote systems or networks.

The patient data repository 107 and the system data repository 108 can be a solid-state drive, hard drive or other memory device. The patient data repository 107 can store patient-related data and treatment parameters, such as patient records, treatment session chronology, and disease documentation and photos. The system data repository 108 stores all system-related data and parameters, such as the system log, x-ray calibration data, and system diagnostics results. The patient data repository 107 and the system data repository 108 can be discrete devices or physically combined. One or more partitions can be used if the repositories 107 and 108 are combined, such as a single repository.

Figure 2:
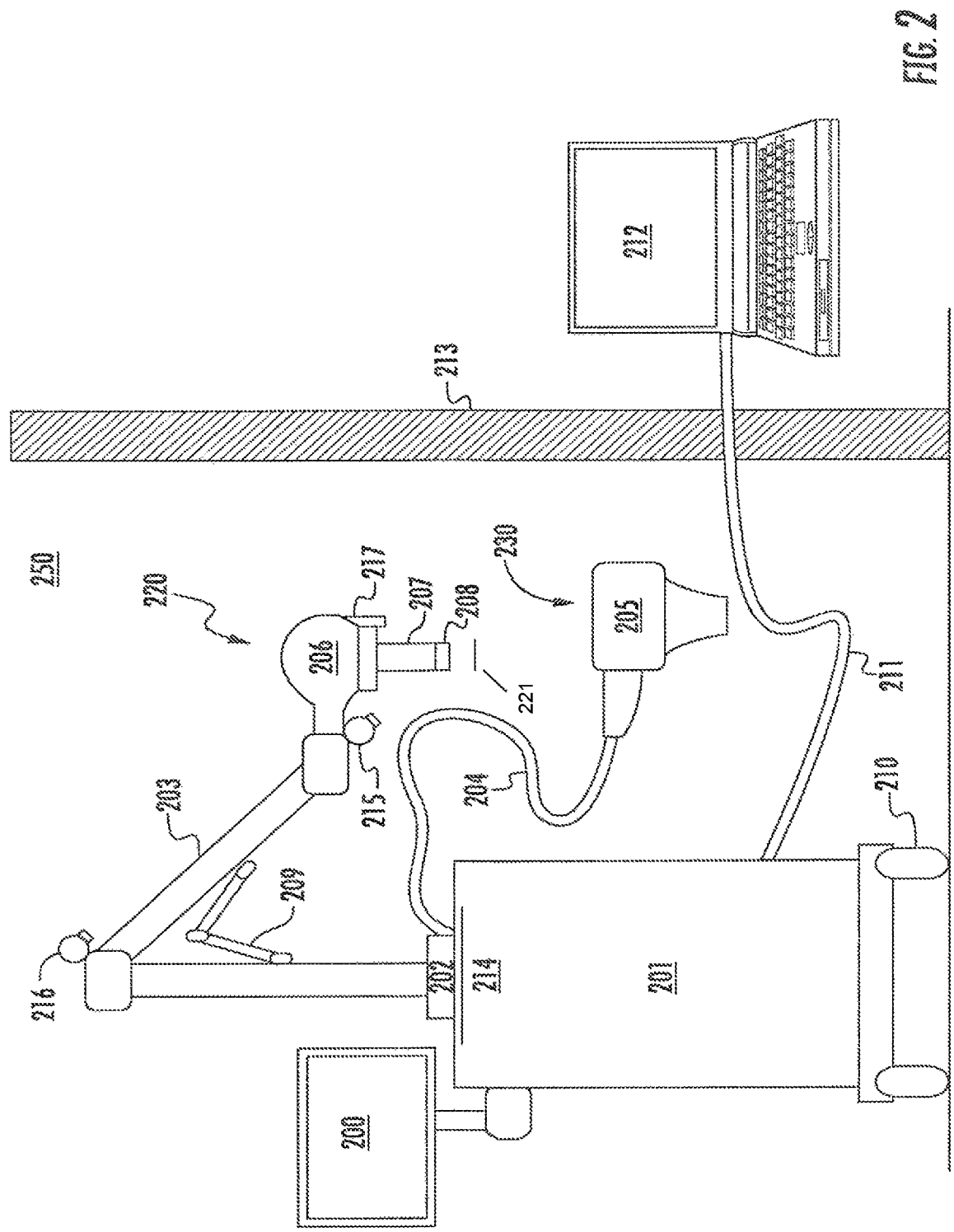
FIG. 2 is an exemplary embodiment of an image-guided radiotherapy system.

One embodiment of an ultrasound guided radio therapy treatment and diagnostic system 250 is shown in FIG. 2. The system 250 can include a base unit 201 with various components mounted thereon or connected therewith. These components can include a radiotherapy treatment device 220 and its various components and an ultrasound imaging device 230.

The a base unit 201 is typically a compact unit such as one with a 30"×30" footprint and can be mounted on casters 210 for ease of maneuverability. The base unit 201 can include a power lead for optionally providing power to all of the components housed in or connected to the base unit 201. In this regard, the base unit 201 can contain one or more computers for controlling the system 250 components and/or analyzing and processing data obtained from the system 250 components. A monitor 200 can also mounted to the base unit 201 for a user interface. Likewise, a terminal or an input device 214, such a as key board or mouse, can be included.

A mount 202 is provided on the base unit 201 for mounting the radiotherapy treatment device 220. The radiotherapy treatment device 220 can include a treatment arm 203 and treatment head 206, which can include removable or movable applicators 207, 208. The treatment arm 203 is articulated with appropriate retractable articulations 209. A camera 216 can also be included to provide for remote operation or for documentation of treatment. A video-laser positioning system having camera 215 and laser or light pointer 217, which visibly marks a region with a crosshair that will receive radiotherapy treatment, can be provided. The camera 215 can capture low opacity images of the radiotherapy treatment head 206 and crosshairs of laser pointer 217 during treatment so that the exact positioning and orientation can be reproduced during subsequent treatments. In this regard, the video-laser positioning system can identify proper and precise positioning and orientation of treatment head 206. The video-laser positioning system can also allow for remote control and operation of the treatment arm 203 so that the treatment head 206 can be positioned precisely while the user is remote. In operation discussed below, the treatment arm 203 can be articulated and positioned to allow the treatment head to apply radiotherapy to a patient.

The ultrasound device 230 can include the ultrasound head 205 attached via a lead 204 to the base unit 201 and data acquisition and processing machinery housed therein. In operation, the ultrasound device 230 can be used to collect images and data of a diagnosis or treatment area before, during or throughout and after treatment. In some arrangements, the ultrasound head 205 can be mounted on the arm 203 instead of being provided separately.

Lead 211 can connect the system 250 to another computer or use interface that can be positioned behind a shield 213 for remote operation of the system 250 or components of system 250, such as the radiotherapy treatment device 220.

Figure 3:
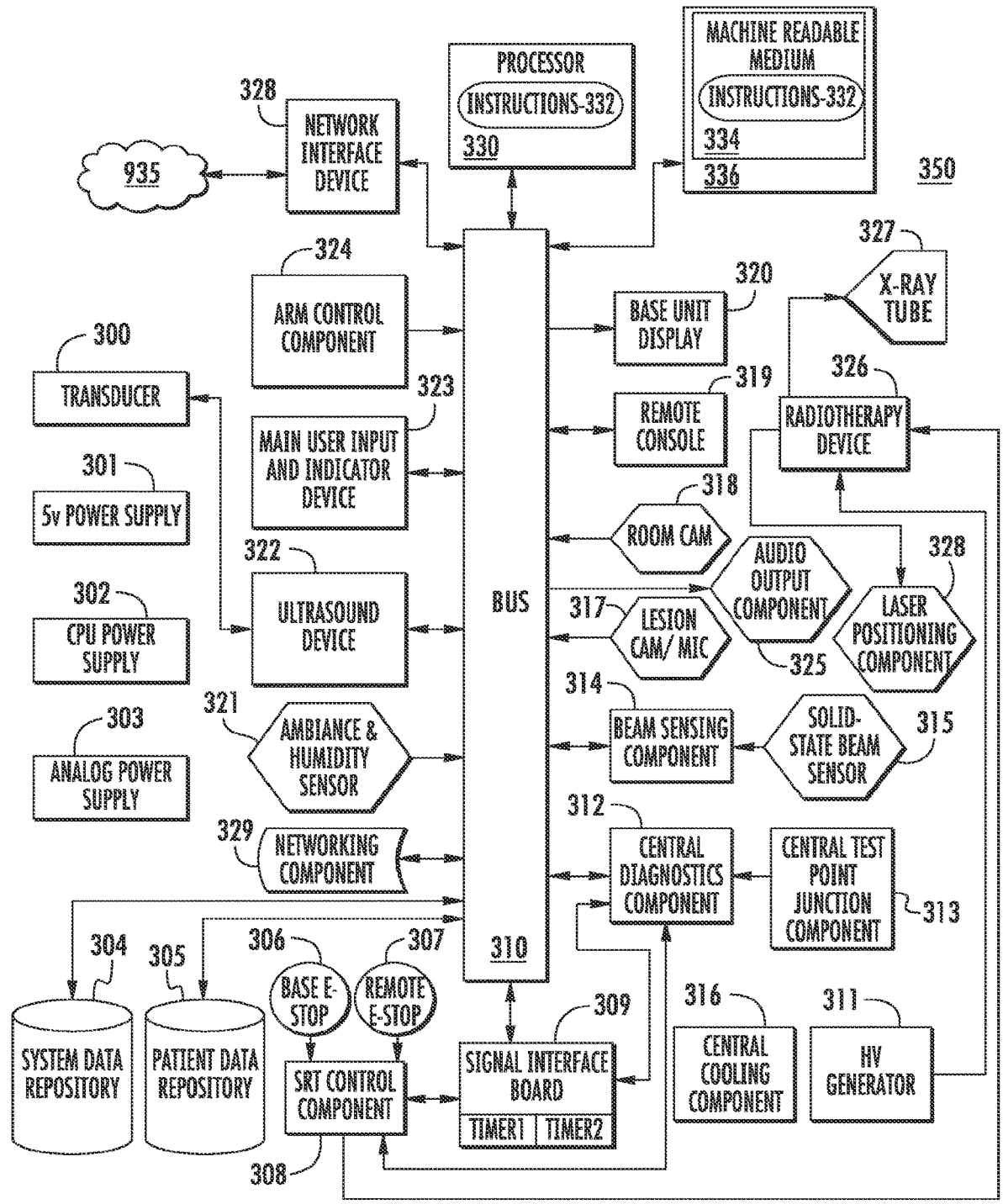
FIG. 3 is a schematic drawing of another embodiment of an image-guided radiotherapy system.

FIG. 3 illustrates a schematic view of various components and sub-components of system 350. The system 350 can include a bus 310 through which the various components can communicate with each other and/or the processor 330 (e.g., a central processing unit (CPU), a graphics processing unit (GPU), or both). The processor 330 can be connected to the bus 310 as shown in FIG. 3 or integrated therewith. Power supplies 301, 302, 303 can also be included.

The system 350 can be controlled and operated by processor 330 that runs the system 350 software or instructions 332, which controls the system 350 functions, verifies the safety mechanisms, and the service and calibration functions. The processor 330 can be in communication with a machine-readable medium 334, which can be static memory 336, on which is stored one or more sets of instructions 332 (e.g., software) embodying any one or more of the methodologies or functions described herein, including those methods illustrated herein. The instructions 332 may also reside, completely or at least partially, within the system data repository 304, static memory, or within the processor 330, or a combination thereof, during execution thereof by the system 350. The system data repository and patient data repository and the processor 330 also may constitute machine-readable media.

The processor 330 can be in communication with a motherboard having an appropriate amount of static or dynamic RAM, such as 4 GB of DRAM, in order to optimally support and accommodate the operating system, main software, and real-time system monitoring functions, together with efficient patient and data system handling and archiving. The system 350 software also communicates with the peripheral components, such as Ethernet, USB, and audio/video or via network interface card 338 in order to implement the system's user/machine interface and exchange data with external workstations and data repositories, such as electronic medical records (EMR), electronic health care records (EHR), hospital information systems (HIS), radiology information system (RIS), and picture archiving and communication systems (PACS), utilizing digital imaging and communications in medicine (DICOM) and health level 7 (HL7) communications and data structure protocols.

The system 350 can include storage mediums 304 and 305, such as solid state drives, hard drives or the like. Storage medium 304 can be the system data repository, which can include the operating system, the main system software, and system data and parameters archive. Storage medium 305 can be the patient data repository 305, which stores all patient-related data and records.

The system 350 can include a base unit that houses or otherwise provides various components of the system 350, including user interfaces. The base unit can include a base unit display device 320, such as an LCD display, and a base unit user input and indicator device 323, such as a terminal or a mouse. The system 350 can also include a remote console 319 that can be used to remotely control the system 350 so that a user does not need to be present during radiotherapy treatment. The base unit user input and indicator device 323 allows the user to interact with the system 350. The base unit user input and indicator device 323 can be utilized for initial patient data setup on the system 350 and for the ultrasound imaging of the patient's tumor at various stages of the disease before, during, and after the superficial radiotherapy period. Furthermore, the base unit user input and indicator device 323 can also be a terminal of the system 350 software. The diagnostics results and images, patient data, remote workstations topology, patient and room monitoring data, system service menus, system physics and calibration menus, and all system queues and alerts can be displayed on the base unit display device 320 or via the base unit user input and indicator device 323 as appropriate.

The system 350 can also include an ultrasound device 322 with a transducer 300. The ultrasound device can obtain images of the treatment area or skin lesion of concern. With the ultrasound device 322 with a transducer 300, diagnostics of the area of concern can be processed. The ultrasound device 322 can be any ultrasound device capable of operating within an acceptable bandwidth. For example, the high frequency ultrasound device 322 can operate in a bandwidth of approximately 20 MhZ to approximately 70 MhZ, and may be implemented with an electro-mechanical, or solid state transducer. The system 350 can provide the ultrasound imaging device 322 at least partially integrated inside a system 350 housing coupled to bus 310 with a transducer head outside of the housing as shown in FIG. 2. The imaging device 322, and other components of the system 350, can be in communication with the bus 310 and the respective other components of the system 350 utilizing interface standards such as peripheral component interconnect (PCI/PCIe), universal serial bus (USB/USBII/USBIII), or Firewire.

The system 350 can further include a radiotherapy device 326 that includes an X-ray tube 327. As discussed herein, the radiotherapy device 326 that includes an X-ray tube 327 can deliver pinpoint radiation therapy to a particular region or area on a patient. The radiotherapy device 326 can be coupled with a high voltage generator 311 and a central cooling component 316.

The system 350 can also include a control component, such as superficial radiotherapy control component 308, for controlling the radiotherapy provided by radiotherapy device 326. The superficial radiotherapy control component 308 can control aspects of the radiation dosage, including timing, depth and intensity. In this regard, an arm control component 324 can also be provided with the system 350 and in communication with the superficial radiotherapy control component 308 and/or processor 330. The arm control component 324 can move, articulate or otherwise control positioning of the arm to which the radiotherapy device 326 and x-ray tube 327 are mounted. A base e-stop 306 and remote e-stop 307 can also be provided to provide local and remote emergency termination functions so that the radiotherapy device 326 can be stopped either locally or remotely.

Additionally, solid state beam sensing component 314 with a solid-state beam sensor 315 can be provided. In one embodiment, these components can be housed within the housing of X-ray tube 327. The solid state beam sensing component 314 with a solid-state beam sensor 315 provide the ability to obtain on demand and local analysis of the radiotherapy device 326 with X-ray tube 327. Utilizing the solid state beam sensing component 314 with a solid-state beam sensor 315, the radiotherapy device 326 with X-ray tube 327 can be tested to determine if the radiation output is consistent with the desired radiation output. In the event that there are discrepancies, the devices can be re-calibrated or otherwise serviced.

A central diagnostics component 312 can also be provided and can be interfaced with bus 310 and processor 330. The central diagnostic component 312 is also connected with a central test point junction conjunction 313 and additionally interfaces with a signal interface board 309 that is in turn connected to both the processor 330 through bus 310 and the superficial radiotherapy control component 308. The signal interface board 309 can also include a first and second timer for redundant time counting during the application of radiation therapy, which provides for added patient safety and accurate dosimetry calculation for the delivered therapy dose to the patient. In addition to the dual hardware timers, one or more additional software based timers can be utilized or invoked by system 350.

The central diagnostics module 312 is a systems diagnostic component that monitors the various system boards and components for failures and/or errors. The central diagnostics module 312 can generate alerts regarding the system status that can either be communicated with the user, or with the system installer or manufacturer for maintenance purposes.

Additional inputs can be connected to the processor 330 through bus 310 including a camera and/or microphone 317, an audio output component 325, such as a speaker, a room camera 318 for taking pictures or video of the patient, treatment areas and/or the treatment process. An ambiance and humidity sensor 321 can also be provided in the event that conditions may affect the treatment or any of the system 350 components. However, the arrangement is not limited in this regard.

Figure 4A:
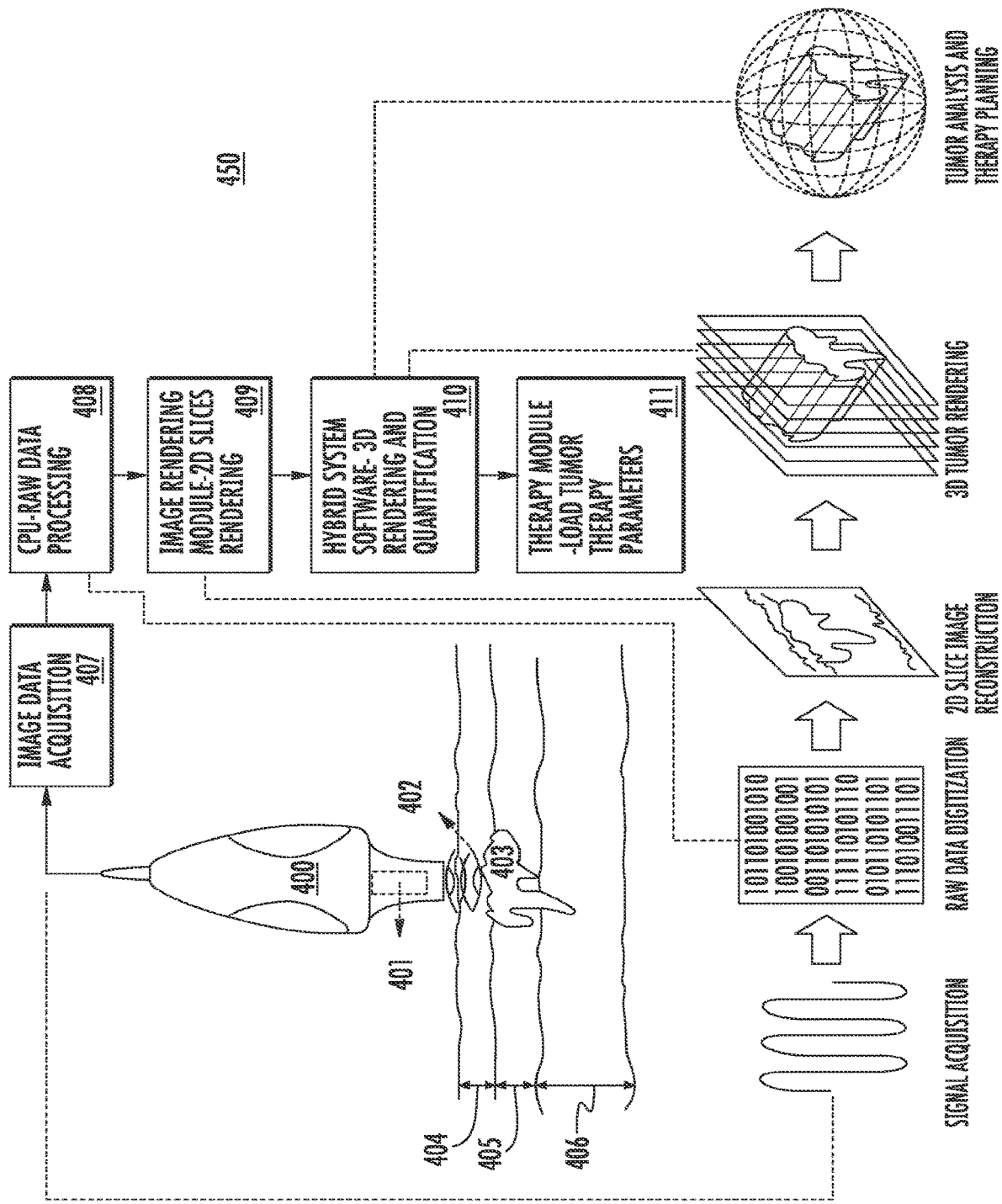
FIG. 4A is a flow diagram of a tumor imaging and quantification process.

FIG. 4A illustrates ultrasound imaging with ultrasound device 400, along with a tumor processing, rendering and analysis method and process 450. As an example, the method and process 450 can be used with systems 150, 250 and 350, and their software that can be integrated with or operatively in communication with various system components as shown in FIGS. 1-3.

In FIG. 4A, an ultrasound head or device 400 includes an ultrasound transducer 401 located in the head 400. High frequency ultrasound is used for the imaging, which provides a much clearer image in comparison to low frequency ultrasound, but which does not penetrate deeply into the skin. High frequency ultrasound can include frequency ranges of approximately 20 MhZ to approximately 70 MhZ, such as approximately 35 MhZ to approximately 55 MhZ.

In operation, the method and process 4540 can begin with obtaining ultrasound image data. The ultrasound beam 402 is aimed at an area of concern, such as lesion 403, through the epidermis 404, dermis 405 and subcutaneous fat 406. In use, the transducer 401 sends high frequency ultrasonic waves towards the epidermis 404, dermis 405, and subcutaneous tissue 406, where the tumor 403 is located in varying depth, circumference, and volume. The reflected ultrasonic waves 402 that hold the tumor's physical characteristic data are acquired by the transducer 401 as illustrated at 412. As an example, a non-melanoma skin cancer lesion 403 is located as shown, and the lesion 403 may extend away from the epidermis 404 and into the subcutaneous fat 406.

Data and images obtained by the ultrasound device 400 are acquired by an image data acquisition component 407 and pre-processed at 413 for further processing, as shown with the flow diagram of FIG. 4A. The image data acquisition component 407 can be operatively in communication with a central processing unit 408, which processes the raw data captured by the image data acquisition module 407. At step 409, the central processing unit 408 can execute instructions of software to process the data to create and render 2-dimensional (2D) images, which are acquired in slices across the area imaged by the ultrasound device 400 as shown at 414.

At step 410, the slices of 2D images are process for rendering one or more 3-dimensional (3D) images of the imaged volume that may include a tumor. Also at 410, a volumetric 3D representation of the tumor can be created, the volume and depth of the tumor can be calculated and the edges of the tumor can be determined. For example, at step 410, the system can operate to capture each rendered 2D image slice 414 that contains cross-sectional tumor data and process the image. The processing can include determining the tumor's edge within each 2D slice. The tumor image for the processed 2D image slice 414 can then be isolated and stored in a respective sequential bin in memory. The processing can continue until a portion or all of the 2D image slices have been processed with the tumor image for each processed 2D image slice 414 isolated and stored in a respective sequential bin in memory. The system can then combine a plurality of all of the tumor images for each processed 2D image slice 414 isolated and stored in a respective sequential bin in memory into a three-dimensional stack, illustrated at 415.

At step 410, a 3D tumor model or volumetric model 416 can be rendered. A 3D construction and rendering engine can combine all or a portion of extracted 2D tumor slices, as shown at 415, in sequence together with their respective slice thickness to merge and fuse them into an integrated 3D model that represents and manifests the tumor's 3D anatomy and volume. During the construction and rendering sequence, the 3D engine can apply geometrical corrections, smoothing and anatomical triangulation to the rendered 3D tumor model in order to achieve a correlation with the actual scanned or imaged tumor.

The 3D tumor model 416 can be passed to the therapy module at 411, which can be hardware or software, for tumor analysis and therapy planning, The therapy module 411 can analyze the 3D tumor topography and calculate the designated treatment area voxel, along with the pertinent dosimetry to be applied by a radiotherapy device. The dosimetry can include measurements and calculations of the absorbed dose in tissue resulting from the exposure to radiation. In one example, the appropriate treatment volume can be a spherical shape as illustrated at 416. Alternatively, the appropriate treatment volume can be any other suitable shape that will leave appropriate treatment margins around the tumor. The accuracy provided by the ultrasound imaging allows the treatment margins to be of the order of 10%, which is a significant improvement over the typical 300% treatment margins used in Mohs surgery.

At step 411, appropriate therapy can be determined using the data and images from 410. The therapy software can include vector tables identifying the appropriate radiotherapy dosages for different sized tumors. An example of such a table is provided at FIG. 4B. This allows the system to precisely calculate therapy parameters, including treatment dosage based on the actual size of the tumor, including its depth and volume, rather than relying on the physician having to estimate the tumor size and depth based on experience and the visible surface area of the tumor.

Figure 5:
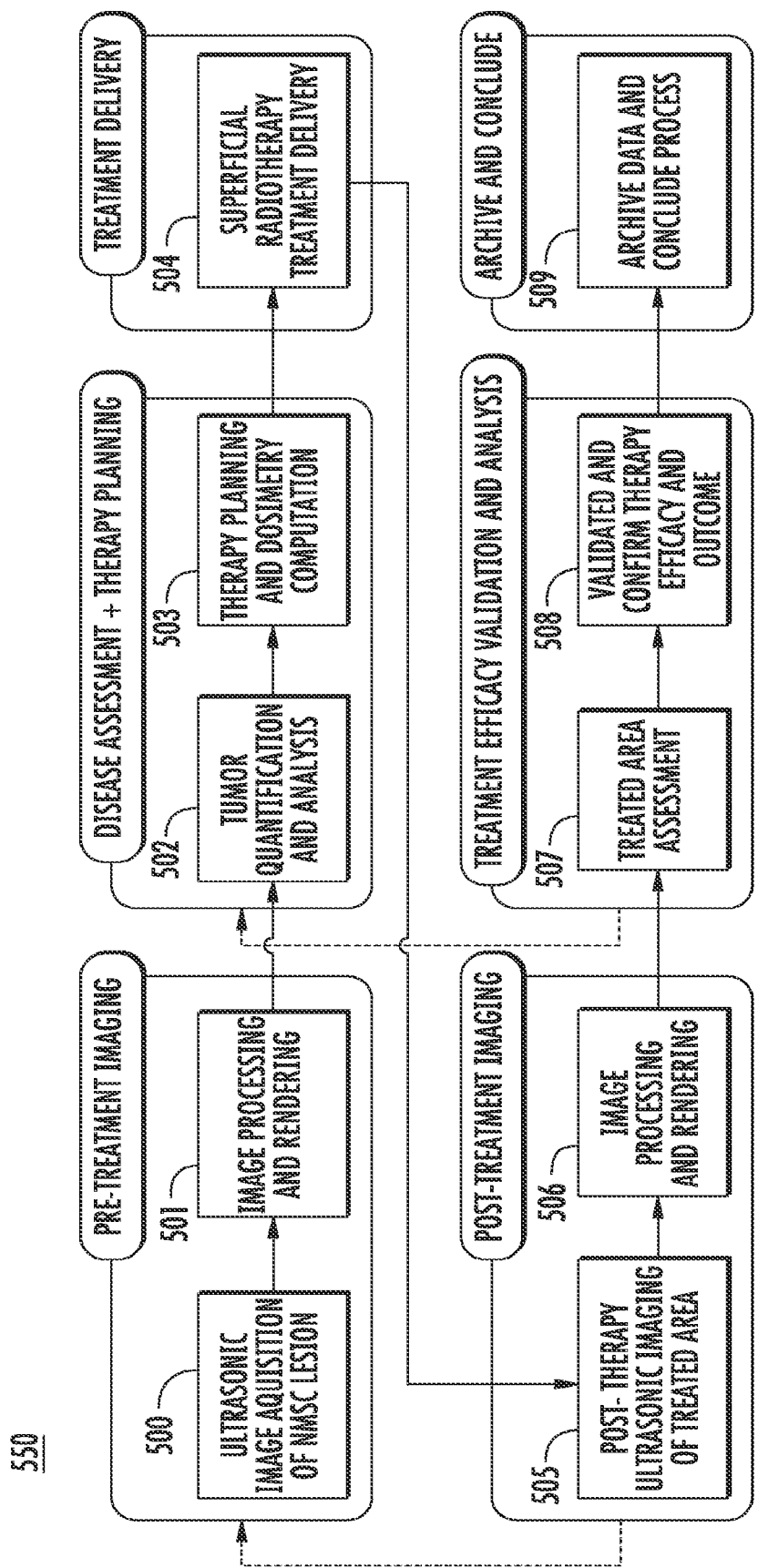
FIG. 5 is flow diagram of a method of diagnosis and treatment.

One embodiment of a method 550 of diagnosis, therapy planning, radiotherapy treatment, post treatment diagnosis and treatment validation and analysis is provided in a flow diagram of FIG. 5. Although the flow diagram illustrates the steps as sequential, the steps can be completed in different logical orders and some steps, or groups of steps, can be repeated as needed.

The method 550 can begin during a pre-treatment imaging stage at step 500 with the ultrasonic image capture of a skin. At step 500, ultrasonic image acquisition of an area of concern, such as a non-melanoma skin cancer (NMSC) lesion, is utilized to acquire the physiological parameters of the lesion or tumor. Acquired data and images are then transferred to the image processing and rendering step 501. As noted above in reference to FIG. 4A and the corresponding discussion, raw image data is subject to image processing and rendering at step 501. At step 501, the lesion or tumor is assessed, defined, quantified, and diagnosed, including any classifications for skin cancer type. The pre-treatment imaging provides a user, such as doctor or clinician, with a local means to diagnose the skin cancer type instead of using the time consuming and invasive biopsy method. The pre-treatment imaging also allows the user and the patient to choose a treatment path for the diagnosed skin cancer type.

Based upon the initial imaging and analysis data, including any classification as to a type of skin cancer, the clinician and patient can decide to proceed with superficial radiotherapy to treat the diagnosed skin cancer lesion. During the disease assessment and therapy planning stage, tumor quantification and analysis step 502 can incur. The tumor can being analyzed by a 3D engine that processes all acquired 2D cross-sectional images, delineates the tumor anatomy within the 2D image slices, and detects the tumor's edge in each processed 2D slice. The processing allows the tumor to be extracted and used discretely for its respective slice number/sequence during the 3D model reconstruction and tumor volume quantification process, as illustrated at 415 and 416 of FIG. 4A. Thus, the step can include the creation of the 3D representation of the tumor and analysis of the suitable treatment volume as described above with respect to 415 and 416.

With a tumor volumetric model, such as tumor volumetric model 416 is reconstructed, rendered, and quantified, therapy planning and dosimetry computation can occur at step 503. Therapy planning and dosimetry computation is carried out at step 503 where the data and images passed from step 502 can be further manipulated and analyzed, including analysis of the tumor and therapy factors. The therapy planning can include not only the dosimetry computation (as described above with reference to the therapy module 411), but also planning for the best location on the skin to reach the center of the tumor and the best angle of presentation for the treatment head. To plan treatment, 3D tumor can be orientated in correlation to the anatomy of the area to be treated. Physiological, topographic, and radiation therapy dosimetry parameters can be applied to compute and design the treatment plan, beam targeting and guidance, including the treated area voxel. A fractionation scheme and treatment head positioning on the patient can also be determined. The treatment plan can completed and loaded into a patient record and scheduler.

At step 504, image-guided radiotherapy treatment fraction can be delivered. A radiotherapy component or device, such as component 220 from FIG. 2 or device 326 from FIG. 3, can be used to deliver treatment according to the treatment plan. Thus, the treatment plan can be read and interpreted and X-ray beam therapy can be delivered accordingly to the designated lesion. In this regard, the X-ray beam therapy is guided by the 3D imaging and dosimetry data from the treatment plan that was specifically created for the patient and the specific skin lesion to be treated.

In one arrangement, the components of the system 250 of FIG. 2 can be used to provide the image-guided radiotherapy treatment of step 504. The treatment head 206 and treatment applicators 307, 308 can be positioned over the patient's area to be treated utilizing the built-in video-laser positioning system 215, 217. The video-laser positioning system operates to align the treated area's video image with a low opacity snapshot of the previous treatment head 206 position together with crosshairs projected by laser 217 that are projected in both real-time and previous snapshot images. The system then ensures that the treated area's video image with laser crosshairs and the low opacity snapshot with the laser crosshairs are aligned together to the exact same position, which ensures an accurate and reproducible treatment head 206 positioning over the treated lesion. Once the treatment head 206 is in place, the user engages the system 250 to deliver the treatment fraction to the lesion. The timing, energy, and geometry of the beam are all guided by the image analysis, 3D tumor modeling, and the derived physics and dosimetry calculations and analysis.

For example, treatment can be provided in multiple, short fractionated treatment sessions. Each treatment fraction or session can be less than one minute long while delivering a dose of approximately 300 cGy to approximately 500 cGy per fraction. Depending on the prescribed total dose, the lesion can be treated with one or more fractions, such as around 12 to around 30 fractions. Additional or less fractions may be used.

A treatment series can include around 5 to around 30 fractions, per the protocol the physician prescribed for a particular lesion condition and state, such as cancer stage one (T1), stage two (T2), etc. Once the lesion is defined and identified, a treatment area is defined for the circumference. This circumference, in turn, can dictate the diameter of the applicator (such as applicators 207, 208 from FIG. 2) that will be used. Generally, the selected applicator for treating a particular lesion circumference can be at least 20% larger in area and/or diameter of the lesion to be treated. The clinician can create a custom lead template (such as template 221 shown in FIG. 2) that will be cut to the size and shape of the lesion with approximately a 15% extra margin, in order to ensure that the entire malignant area will be impacted by the x-ray beam. All healthy cells that will be exposed to the x-ray beam will generally successfully recover and regenerate, while the malignant cells will go through an apoptosis from which they will not recover.

The template (such as template 221 shown in FIG. 2) can be placed over the lesion, with the cut hole in the center of the treated area, and the selected applicator will be latched onto the x-ray tube head. The treatment system can be set with the pertinent energy level and time span of the treatment (e.g., approximately 20 seconds to approximately 40 seconds), which are defined by vector tables, per the particular lesion's condition and fractionation scheme. The clinician can set the x-ray tube head vis-a-vis the applicator in position and can energize the system from the remote console, outside of the treatment room. The system can deliver the selected energy for the set time and can terminate treatment once the timers count to zero. The patient can be released and summoned for the next scheduled treatment session or fraction.

As will be discussed below, image-guided radiotherapy treatment step 504 can be repeated, but can be revised as needed. For instance, over the course of a treatment, a non-uniform shaped tumor may decrease in depth, width and overall size. Iterative treatments can be reduced in treatment size or intensity so that only the necessary amount of radiation is applied to as small a region as possible.

The method 550 can then move on to the post treatment imaging phase. The post treatment imaging phase can be an iterative lesion imaging procedure that is completed after the previous imaging and assessment of the lesion. Post treatment imaging provides the ability to track and evaluate the therapy progression and healing process of the treated lesion during the fractionated therapy process. The interval of the lesion imaging is determined by the clinician according to the protocol illustrated in FIG. 7 and discussed further below.

At step 505, the treated area can again be imaged with an ultrasound device, such as ultrasound device 400 of FIG. 4A. During step 505, the actions and operations of step 500 can be repeated. Thus, step 505 can include an ultrasonic scan of the treated area after the first and subsequent therapy fractions in order to gather up-to-date image data of the treated lesion.

The post treatment images and data of the treated lesion can be processes and further images can be rendered in step 506. During step 506, the actions and operations of step 501 can be repeated.

The method 550 can move to the treatment efficacy validation and analysis of steps 507 and 508, which provide for an iterative analysis of the lesion's topography and volume over time throughout the span of treatment and upon treatment completion, during the follow-up sessions. At step 507, the post treatment images and data from steps 505 and 506 can be assessed to determine how the legion responds to therapy in comparison to the anticipated healing rate, according the prescribed dosimetry and fractionation scheme of the treatment plan. Step 507 can include one or more of the actions or operations of step 502 to fully analyze a tumor or lesion.

As an example, the newly acquired images and data indicates non-responsiveness, the treatment plan or other factors can be reviewed. In this regard, step 503 can be repeated where the treatment plan can be changed based on the post treatment imaging and assessment. On the other hand, if the newly acquired images and data indicates responsiveness, the treatment plan can be confirmed and treatment can progress. The steps provide an ongoing treated lesion assessment throughout the treatment and at its completion to evaluate the lesion evolution and its response to the therapy. The post treatment analysis can also be during the post-treatment follow-up sessions of the patient in order to document and validate or verify the full recovery and healing of the skin cancer lesion in the treated area.

Step 508, validation and confirmation of therapy efficacy and outcome can obtained. Step 508 can include image triangulation as a function of time and volume. By triangulating the 2D or 3D images, the size and shape of the tumor or lesion can be tracked. Also, volumetric analysis of the tumor over time can also be completed. The changes in the size, shape and volume of the tumor can be compared reviewed to determine effectiveness of the treatment, while factoring parameters of tumor transmutation and response to therapy. Thus, the clinician obtains an ongoing accurate assessment of the patient's response to therapy and can adjust the therapy if necessary in order to further optimize the patient's outcome. For instance, treatment session lengths or intensity can be decrease or increased. Step 508 can be completed locally by the clinician in a non-invasive manner, without any discomfort to the patient or the necessity for ancillary lab and pathology services.

At step 509, patient records can be stored and the method 550 completed. The records can include patient record data and images, results, and summary reports that illustrate the patient's disease state from procedure commencement to its ultimate conclusion. The records can be stored to local and networked record storage repositories.

Any of the steps can be repeated as needed. For instance, a tumor may require multiple treatment sessions before treatment is completed. The imaging steps, assessment and planning steps and the treatment steps may be repeated multiple times.

As all of these steps can be carried out with a single machine in a physician's office, this greatly cuts down the time, inconvenience and expense associate with diagnosis and treatment of non-melanoma skin cancer. Additionally, as it reduces or even removes the need for Mohs surgery, the patient's subsequent healing time and scarring is much reduced.

Figure 6:
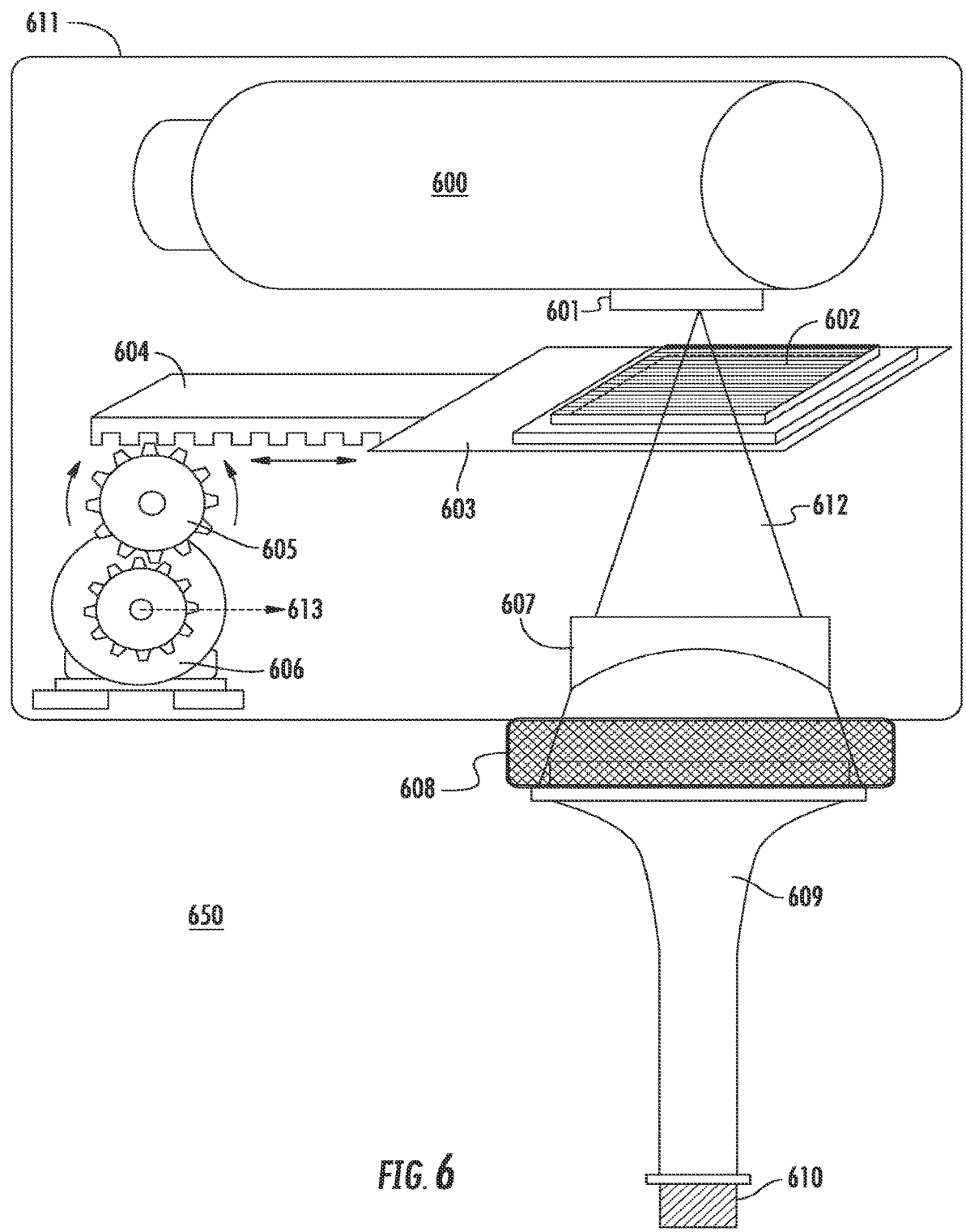
FIG. 6 is an exemplary embodiment of a beam sensing component.

Turning to FIG. 6, a solid state beam sensor and beam sensing component 650, such as solid state beam sensor 313 and beam sensing component 312 of FIG. 3, or solid-state X-ray beam sensing component 102 of FIG. 1, can be provided. These components can be incorporated in an X-ray tube housing 611, such as the X-ray tube in treatment head 206 of FIG. 2.

The component or device 650 can include retractable support structure 603, 604 that can also be incorporated in X-ray tube housing 611. Also provided can be a x-ray imaging array detector, such as solid-state x-ray detector array 602, which is located between the X-Ray tube 600 with x-ray tube alignment 601, and a Bremmstrahlung beam-hardening aluminum filter 607. The solid-state detector array 602 that is mounted on the retractable support structure 603 can be utilized to sense the x-ray beam 612 output from the x-ray tube 600.

The retractable support structure 603 can move the solid-state detector array 602 between an X-ray testing position, as shown in FIG. 4A, and a non-testing position. In the non-testing position, the solid-state detector array 602 and/or the retractable support structure 603 is retracted or moved away from the field of emitted x-rays such that they do not absorb, block or otherwise interfere with radiation beams that are emitted from x-ray tube 600.

When the x-ray beam 612 is detected, the solid-state detector array 602 can sense characteristics of the radiation emitted from the x-ray tube 600. The detector array 602 can be used to generate a matrix-like image of the circumference of X-ray beam 612, together with the intensity of the x-ray beam's particles.

The x-ray imaging array detector can be a one-line array or a matrix array of solid state x-ray detectors that acquire and gather characteristics of the beam during the a check or testing procedure. One characteristic is the beam shape integrity, which validates that the x-ray tube output is indeed homogenous and without flaws. Another characteristic is the beam intensity that can be measured by centigray (cGy), or kilovoltage (Kv) units. Other characteristics sensed by the x-ray imaging array detector include the cross section or shape of the beam. The x-ray imaging array detector can also accurately measure the photons emitted from the x-ray tube 600. Further, the x-ray imaging array detector can also be used to determine whether the x-ray tube port 601 is properly aligned or if realignment is needed.

The collected data can be communicated to the beam sensing component, such as beam sensing component 312 of FIG. 3, that pre-processes the data. The pre-processed data can be communicated with a processor, such as processor 330, for further analysis and visualization. The solid state beam sensor and beam sensing component can be utilized as a daily quality control tool and for overall system diagnosis purposes. For instance, the solid state beam sensor and beam sensing component may detect a difference between the programmed radiation and what is output from the X-ray tube 600. Detection can allow for maintenance to ensure desired treatment dosages are delivered. Still further, testing can be automated before use such that the emitted x-rays and/or alignment of the x-ray tube port 601 is confirmed prior to each use.

The retractable support structure 603, 604 can include at least one motor or actuator 613 and positioning components 605, 606. The motor or actuator 613 can be controlled via a processor, such as processor 330 with the beam sensing component 314. The motor or actuator 613 can move the solid-state detector array 602 between the X-ray testing position and the non-testing position.

FIG. 6 also shows a removable treatment head 609 with tip 610 that can be changed to suit the treatment area and depth needed. Suitable treatment heads that may be used in the component 650 can include treatment applicators, ranging from approximately 1 cm through approximately 7.3 cm diameter heads at approximately 15 cm SSD, and also approximately 1 cm through approximately 12.7 cm diameter heads at approximately 25 cm SSD. The removable head 609 can be used with radiotherapy devices 220 and 326.

FIG. 7 provides a flow chart of patient and treatment management protocol 750. When a patient first arrives at a doctor or clinician, the patient acceptance and consultation step 700 can occur. In this step, the patient is registered in the practice's workflow management system that can be integrated with a hybrid image-guided superficial radiotherapy system that can employ protocols such as DICOM and HL7, such as the system 350 illustrated at FIG. 3 or any suitable system.

With registration, the patient can be scheduled for the initial prognosis and consultation with the clinician. During initial prognosis and consultation, the patient can be scanned by an ultrasonic device, as part of the image guidance phase 707. The scanning provides the clinician and the patient an assessment of any lesions and the disease state before making a decision on the recommended and preferred treatment path. The scanned lesion image data is then processed and reconstructed at step 702 to render the 2D image slices of the scanned area that contain the 2D cross-sections of the tumor. If desired, these images can be reviewed. The 2D tumor data can also converted to a 3D volumetric model and rendered to derive all the volumetric and physiological data of the tumor out of the scanned lesion, all for use in the next step.

Treatment planning step 703, uses the quantified data to calculate and generate a personalized treatment plan for the patient and the treated lesion.

Therapy can then commence at step 704, while imaging is still being applied 708 in varying intervals according to the clinician's and treatment plan's protocol to monitor and guide the course of the therapy throughout the prescribed fractions and entire treatment span.

Patient follow-up sessions 705 can be conducted to verify and monitor the full recovery of the treated lesion. As an example, follow-up sessions can be completed months or years after the last therapy session to monitor the area of a treated lesion. This stage is also being image-guided 709 with images obtained with a high frequency ultrasound device in order to add further validity to the treatment's outcome and to verify that indeed the lesion is completely cured and gone.

When the entire therapy sequence is complete at step 706, the patient data and all pertinent image-guidance data 710 is archived and submitted to the medical record management systems and the healthcare management systems. By generally the entire treatment process including non-invasive imaging as a substitute to invasive, time consuming, and expensive biopsies, the patient management protocol is being dramatically enhanced and improved, which offers benefits to all entities and parties involved, including the patient, the clinician, and the healthcare system as a whole.

Figure 8A:
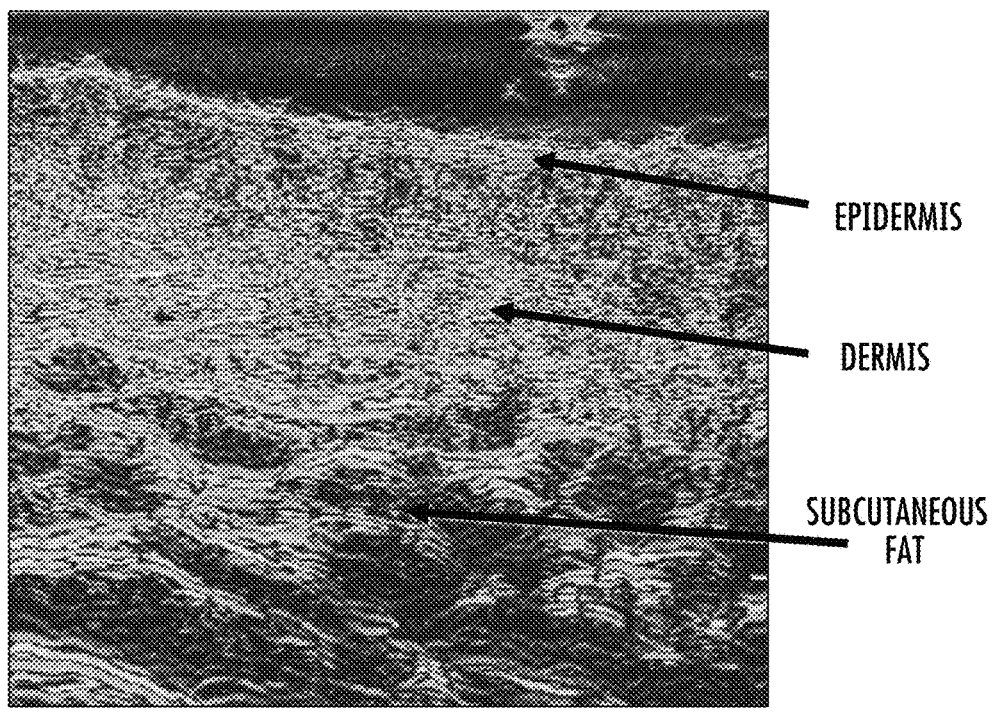
FIGS. 8A and 8B are exemplary imaging results.
Figure 8B:
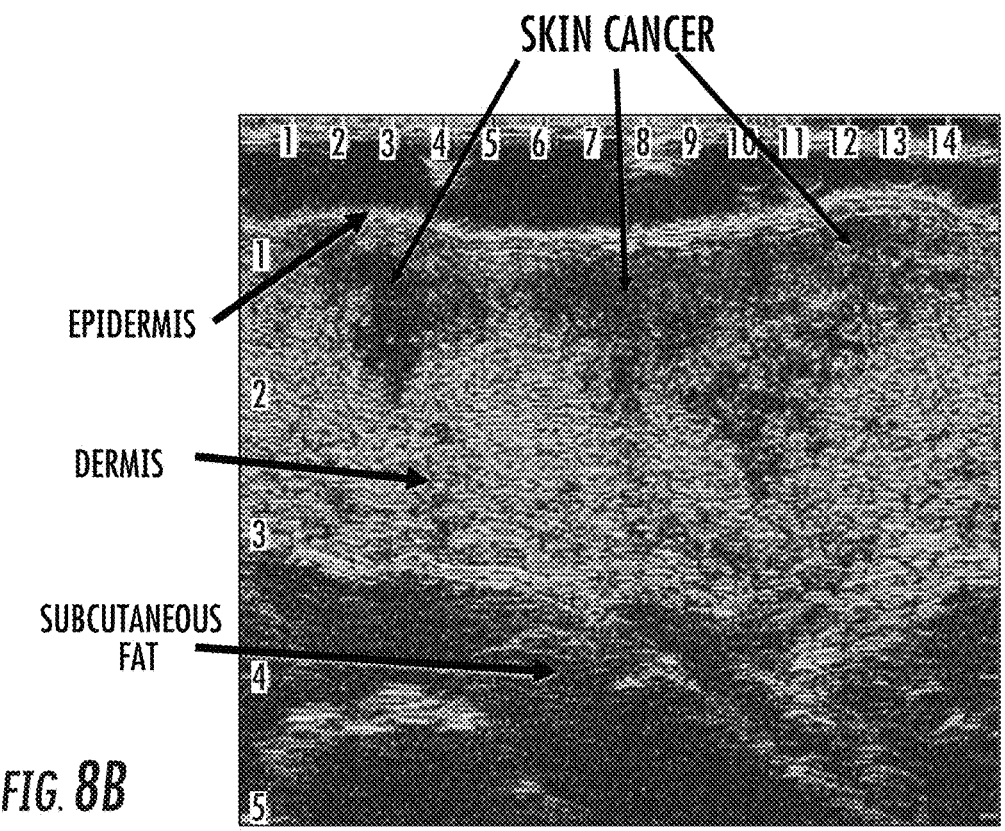

FIGS. 8A and 8B shows two examples of the imaging produced at 40 MHz, with no skin cancer detected in FIG. 8A and three possible areas of cancerous tissue shown just below the surface of the epidermis in FIG. 8B. Such images are exemplary of the images that can be obtained pre and post treatment. They illustrate that the cancerous tissue can be of non-uniform shape, overall size, width and depth. With the understanding of these dimensions and shapes, pinpoint radiotherapy treatment can be provided.

The systems, methods and devices include broader applications beyond treating lesions or skin cancer. For instance, the systems, methods and devices can be utilized as intra operative radiotherapy in surgical environments to treat other cancers or lesions when their respective tumors are surgically removed. In addition to removal of a tumor, an excised area can imaged, analyzed and treated with the systems, methods and devices herein, such as treating an excised area with one or more 21 Gy fractions before the patient is sutured.

The present systems, devices, methods and protocols provide many advantages and improvements for the treatment of skin cancer. In particular, the realization that high frequency ultrasound can be used for accurate imaging of skin lesions, and for treatment planning allows for much greater treatment accuracy. Additionally, it allows for superficial radiotherapy to be used in a much more precise and skillful manner than has hitherto been possible, and reduces or even removes the need for Mohs surgery. Finally, the precise imaging and rendering of tumors means that it is no longer necessary for a physician to have to biopsy suspicious lesions.

In some arrangements, the systems, devices, methods and protocols can be employed for relatively superficial tumors that are not skin cancers, such as certain breast cancers, in which case the treatment head can include a surgical catheter for insertion beneath the skin, together with a small scale spherical treatment head.

It is important to note that the methods described above may incorporate any of the functionality, devices, and/or features of the systems described above, or otherwise, and are not intended to be limited to the description or examples provided herein.

Referring now also to FIG. 9, at least a portion of the methodologies and techniques described with respect to the exemplary embodiments can incorporate a machine, such as, but not limited to, computer system 900, or other computing device within which a set of instructions, when executed, may cause the machine to perform any one or more of the methodologies or functions discussed above. The machine may be configured to facilitate various operations conducted by the systems illustrated at FIGS. 3 and 4. For example, the machine may be configured to, but is not limited to, assist these systems by providing processing power to assist with processing loads experienced in the systems, by providing storage capacity for storing instructions or data traversing the systems, or by assisting with any other operations conducted by or within the systems.

In some embodiments, the machine operates as a stand-alone device. In some embodiments, the machine may be connected (e.g., using a network 935) via a network interface, such as network interface 328, to and assist with operations performed by other machines, such as, but not limited to, the radiotherapy device 326, central diagnostics component 312, the data repositories 304 and 305, the SRT control component 308 or the other devices and components of the system at FIG. 3, including any combination thereof. The machine may be connected with any component in the system at FIG. 3. In a networked deployment, the machine may operate in the capacity of a server or a client user machine in server-client user network environment, or as a peer machine in a peer-to-peer (or distributed) network environment. The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The computer system 900 may include a processor 902 (e.g., a central processing unit (CPU), a graphics processing unit (GPU, or both), a main memory 904 and a static memory 906, which communicate with each other via a bus 908. The computer system 900 may further include a video display unit 910 (e.g., a liquid crystal display (LCD), a flat panel, a solid state display, or a cathode ray tube (CRT)). The computer system 900 may include an input device 912 (e.g., a keyboard), a cursor control device 914 (e.g., a mouse), a disk drive unit 916, a signal generation device 918 (e.g., a speaker or remote control) and a network interface device 920.

The disk drive unit 916 may include a machine-readable medium 922 on which is stored one or more sets of instructions 924 (e.g., software) embodying any one or more of the methodologies or functions described herein, including those methods illustrated above. The instructions 924 may also reside, completely or at least partially, within the main memory 904, the static memory 906, or within the processor 902, or a combination thereof, during execution thereof by the computer system 900. The main memory 904 and the processor 902 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine readable medium 922 containing instructions 924 so that a device connected to the communications network 95 can send or receive voice, video or data, and to communicate over the network 935 using the instructions. The instructions 924 may further be transmitted or received over the network 935 via the network interface device 1320.

While the machine-readable medium 1322 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; or other self-contained information archive or set of archives is considered a distribution medium equivalent to a tangible storage medium. In one embodiment, the machine readable storage medium may be a machine readable storage device or a computer readable device. Accordingly, the disclosure is considered to include any one or more of a machine-readable medium or a distribution medium, as listed herein and including art-recognized equivalents and successor media, in which the software implementations herein are stored.

The illustrations of arrangements described herein are intended to provide a general understanding of the structure of various embodiments, and they are not intended to serve as a complete description of all the elements and features of apparatus and systems that might make use of the structures described herein. Many other arrangements will be apparent to those of skill in the art upon reviewing the above description. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific arrangements have been illustrated and described herein, it should be appreciated that any arrangement calculated to achieve the same purpose may be substituted for the specific arrangement shown. This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

The foregoing is provided for purposes of illustrating, explaining, and describing embodiments of this invention. Modifications and adaptations to these embodiments will be apparent to those skilled in the art and may be made without departing from the scope or spirit of this invention. Upon reviewing the aforementioned embodiments, it would be evident to an artisan with ordinary skill in the art that said embodiments can be modified, reduced, or enhanced without departing from the scope and spirit of the claims described below.

The invention claimed is:

1. A system for radiation treatment of skin lesions, comprising:
  a compact maneuverable base unit comprising at least one processor for performing data acquisition and processing operations to facilitate radiation therapy planning and treatment;
  a high-frequency ultrasound imaging device tethered to the base unit via a lead, the high frequency ultrasound imaging device configured to scan and acquire imaging data concerning the anatomy and topology of a patient's skin, and to communicate imaging data to the at least one processor, said high frequency ultrasound device configured to operate at an ultrasound frequency in the range of from 20 MHz to 70 MHz to facilitate imaging of a lesion present exclusively within at least one of a plurality of skin layers selected from the group consisting of the epidermis, dermis, and subcutaneous skin layers;
  the at least one processor configured to execute instructions stored in memory to perform operations, the operations comprising:
    receiving a plurality of two-dimensional image slices from the high-frequency ultrasound imaging device, each image slice extending through the plurality of skin layers;
    isolating the lesion within the skin layers including lesion edges in each of the plurality of two-dimensional image slices to yield a plurality of processed image slices;
    combining at least a portion of the plurality of processed image slices to render a three dimensional model of the lesion including the sub-surface portions of the lesion and sub-surface lesion edges contained within the plurality of skin layers;
    analyzing the three dimensional model of the lesion within the plurality of skin layers to determine lesion type, lesion volume, lesion edges and lesion depth;
    determining a treatment dosimetry based at least on the lesion type, lesion volume, lesion edges and lesion depth, the treatment dosimetry comprising dose energy level, dose amount, dose location and three dimensional dose boundaries defined within the plurality of skin layers; and a radiotherapy device mounted to the compact maneuverable base unit and operable under the control of the at least one processor, the radiotherapy device including a treatment arm and a treatment head, the treatment arm articulated to facilitate positioning of the treatment head at a location to provide radiotherapy treatment to the lesion based on the treatment dosimetry, and the treatment head responsive to the at least one processor to provide the radiotherapy treatment according to the dose energy level, dose amount, dose location and three-dimensional dose boundaries defined by the treatment dosimetry, the radiotherapy treatment comprising an x-ray beam, the x-ray beam having a source beam shape emanating from the treatment head; and at least one positioning system configured to obtain positioning data and to align the treatment head in accordance with the dose location and the three-dimensional dose boundaries for the lesion, the processor storing the positioning data and retrieving the positioning data such that the alignment of the treatment head can be reproduced during successive treatments.

2. The system of claim 1, further comprising:
a camera coupled to the articulating arm;
a laser pointer coupled to the radiotherapy device; and
wherein the camera and laser pointer provide a video-laser positioning system.

3. The system of claim 1, further comprising:
a solid-state x-ray detector array housed within the radiotherapy device to sense characteristics of radiation emitted by the x-ray tube.

4. The system of claim 3, wherein operations further comprise:
testing the radiotherapy device with the solid-state x-ray detector array;
determining characteristics of radiation emitted by the x-ray tube based on the testing of the radiotherapy device; and
adjusting the radiotherapy device based on characteristics of the radiation emitted by the x-ray tube.

5. The system of claim 1, further comprising at least one template configured according to the treatment dosimetry to be placed over the lesion to confine the x-ray beam shape from the source beam shape emanating from the treatment head to a second, treatment beam shape different from the source beam shape.

6. The system of claim 5, wherein the template is configured to provide a treatment margin for applying the radiation to the lesion of between 10 and 15 percent.

7. A system for use in radiation treatment of skin lesions present exclusively within at least one of a plurality of skin layers selected from the group consisting of the epidermis, dermis, and subcutaneous skin layers, comprising:
a memory that stores instructions; and
a processor that executes the instructions to perform operations, the operations comprising:
receiving a plurality of two-dimensional image slices of a lesion from a high-frequency ultrasound imaging device, each image slice extending through the plurality of skin layers;
isolating the lesion within the skin layers in each of the plurality of two-dimensional image slices to yield a plurality of processed images;
combining at least a portion of the plurality of processed image slices to render a three dimensional model of the lesion, including the sub-surface portions of the lesion and sub-surface lesion edges contained within the plurality of skin layers;
analyzing the three dimensional model of the lesion within the plurality of skin layers to determine lesion type, lesion volume, lesion edges and lesion depth;
determining a treatment dosimetry based at least on the lesion type, lesion volume, lesion edges and lesion depth, the treatment dosimetry comprising dose energy level, dose amount, dose location and three-dimensional dose boundaries defined within the plurality of skin layers; and
providing the treatment dosimetry for use with a radiotherapy device.

8. The system of claim 7, wherein the operations further comprise:
receiving solid-state x-ray detector array testing data of the radiotherapy device; and
determining characteristics of radiation emitted by the x-ray tube based on the testing of the radiotherapy device.

9. The system of claim 8, wherein the operations further comprise adjusting the radiotherapy device based on characteristics of the radiation emitted by the x-ray tube.

10. The system of claim 7, wherein the operations further comprise:
analyzing a volume of the lesion after providing the treatment; and
determining a treatment voxel for the volume with the lesion to be treated.

11. A computer-readable device comprising instructions, which when executed by a processor, cause the processor to perform operations comprising:
receiving a plurality of two-dimensional image slices of a skin lesion present exclusively within at least one of a plurality of skin layers selected from the group consisting of the epidermis, dermis, and subcutaneous skin layers, the image slices being received from a high-frequency ultrasound imaging device, each image slice extending through the plurality of skin layers;
isolating the lesion within the skin layers in each of the plurality of two-dimensional image slices to yield a plurality of processed images;
combining at least a portion of the plurality of processed image slices to render a three dimensional model of the lesion, including the sub-surface portions of the lesion and sub-surface lesion edges contained within the plurality of skin layers;
analyzing the three dimensional model of the lesion within the plurality of skin layers to determine lesion type, lesion volume, lesion edges and lesion depth;
determining a treatment dosimetry based at least on the lesion type, lesion volume, lesion edges and lesion depth, the treatment dosimetry comprising dose energy level, dose amount, dose location and three-dimensional dose boundaries defined within the plurality of skin layers; and
providing the treatment dosimetry for use with a radiotherapy device.

12. The computer-readable device of claim 11, wherein the operations further comprise:
receiving solid-state x-ray detector array testing data of the radiotherapy device; and
determining characteristics of radiation emitted by the x-ray tube based on the testing data of the radiotherapy device.

13. The computer-readable device of claim 12, wherein the operations further comprise adjusting the radiotherapy device based on characteristics of the radiation emitted by the x-ray tube.

14. The computer-readable device of claim 11, wherein the operations further comprise determining a treatment voxel for a volume with the lesion to be treated.

15. A method of treating a skin lesion, comprising:
obtaining a plurality of two-dimensional image slices of a skin lesion present exclusively within at least one of a plurality of skin layers selected from the group consisting of the epidermis, dermis, and subcutaneous skin layers, the image slices being received from a high-frequency ultrasound imaging device, each image slice extending through the plurality of skin layers with a high-frequency ultrasound device;
processing, by utilizing instructions stored in memory and executed by a processor, the plurality of two-dimensional image slices to isolate within the skin layers the lesion and yield a plurality of processed images;
combining at least a portion of the plurality of processed image slices to render a three dimensional model of the lesion, including the sub-surface portions of the lesion and sub-surface lesion edges contained within the plurality of skin layers;
analyzing the three dimensional model of the lesion within the plurality of skin layers to determine lesion type, lesion volume, lesion edges and lesion depth;
determining a treatment dosimetry based at least on the lesion type, lesion volume, lesion edges and lesion depth, the treatment dosimetry comprising dose energy level, dose amount, dose location and three-dimensional dose boundaries defined within the plurality of skin layers; and
providing a targeted radiotherapy to the lesion based on the treatment dosimetry, the targeted radiotherapy including the step of providing a radiotherapy device mounted to a compact maneuverable base unit and operable under the control of the at least one processor, the radiotherapy device including a treatment arm and a treatment head, the treatment arm articulated to facilitate positioning of the treatment head at a location to provide radiotherapy treatment to the lesion based on the treatment dosimetry, and the treatment head being responsive to the at least one processor to provide the radiotherapy treatment according to the dose energy level, dose amount, dose location and three-dimensional dose boundaries defined by the treatment dosimetry, the radiotherapy treatment comprising an x-ray beam, the x-ray beam having a source beam shape emanating from the treatment head.

16. The method of claim 15, further comprising:
obtaining a plurality of post radiotherapy treatment images of the lesion with the high-frequency ultrasound device after providing the targeted radiotherapy to the lesion and during a treatment period of time; and
providing further targeted radiotherapy to the lesion based on the plurality of post radiotherapy treatment images of the lesion; and
providing at least one positioning system configured to obtain positioning data and to align the treatment head in accordance with the dose location and the three-dimensional dose boundaries for the lesion, the processor storing the positioning data and retrieving the positioning data such that the alignment of the treatment head can be reproduced during successive treatments.

17. The method of claim 15, further comprising:
wherein providing a targeted radiotherapy to the lesion includes a plurality of sessions of providing the targeted radiotherapy to the lesion over the treatment period of time;
analyzing topography of the lesion intermittently during the treatment period of time.

18. The method of claim 17, further comprising analyzing the lesion volume intermittently during the treatment period of time.

19. The method of claim 15, further comprising determining a treatment voxel for a volume with the lesion to be treated.

20. The method of claim 15, further comprising the step of providing at least one template configured according to the treatment dosimetry, and placing the template over the lesion to confine the x-ray beam shape from the source beam shape emanating from the treatment head to a second, treatment beam shape different from the source beam shape.

21. The method of claim 20, wherein the template is configured to provide a treatment margin for applying the radiation to the lesion of between 10 and 15 percent.

* * * * *